(12) United States Patent
Takayanagi et al.

(10) Patent No.: US 8,227,506 B2
(45) Date of Patent: Jul. 24, 2012

(54) BENZAMIDINE COMPOUND

(75) Inventors: Masaru Takayanagi, Kawasaki (JP); Shunji Takehana, Kawasaki (JP); Kayo Otani, Kawasaki (JP); Yuki Saitou, Kawasaki (JP)

(73) Assignee: Ajinomoto., Inc., Tokyo (JP)

( * ) Notice: Subject to any disclaimer, the term of this patent is extended or adjusted under 35 U.S.C. 154(b) by 1268 days.

(21) Appl. No.: 11/832,895

(22) Filed: Aug. 2, 2007

(65) Prior Publication Data
US 2008/0021065 A1 Jan. 24, 2008
US 2010/0105731 A2 Apr. 29, 2010

Related U.S. Application Data

(63) Continuation of application No. PCT/JP2006/302202, filed on Feb. 2, 2006.

(30) Foreign Application Priority Data

Feb. 2, 2005 (JP) ................... 2005-026949

(51) Int. Cl.
*A61K 31/454* (2006.01)
*C07D 207/06* (2006.01)

(52) U.S. Cl. ..... 514/428; 514/318; 546/194; 548/335.5; 548/347.1; 548/348.1

(58) Field of Classification Search .......... 514/318, 514/428; 546/194; 548/569, 335.5, 347.1, 548/348.1
See application file for complete search history.

(56) References Cited

U.S. PATENT DOCUMENTS

| | | | |
|---|---|---|---|
| 6,683,215 B2 * | 1/2004 | Chucholowski et al. ..... | 564/307 |
| 6,750,342 B1 * | 6/2004 | South et al. ................... | 544/319 |
| 6,784,191 B2 * | 8/2004 | Yoshida et al. ............... | 514/318 |
| 6,812,231 B2 * | 11/2004 | Nakagawa et al. .......... | 514/256 |
| 6,828,338 B2 * | 12/2004 | South et al. ................... | 514/352 |
| 6,835,739 B2 * | 12/2004 | Zhu et al. ..................... | 514/318 |

(Continued)

FOREIGN PATENT DOCUMENTS

EP 0 976 722 A1 2/2000

(Continued)

OTHER PUBLICATIONS

King "Bioisoster . . . " Med. Chem. Principle and Practice, p. 206-209 (1994).*

(Continued)

*Primary Examiner* — Celia Chang
(74) *Attorney, Agent, or Firm* — Oblon, Spivak, McClelland, Maier & Neustadt, L.L.P.

(57) ABSTRACT

Compounds represented by formula (1) and pharmaceutically acceptable salt thereofs:

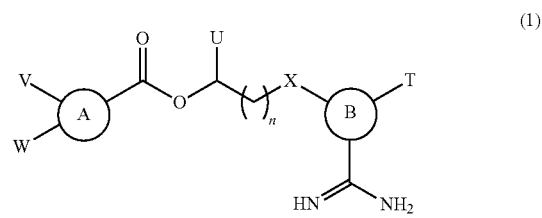

(1)

wherein each symbol is as defined in the specification, are useful as inhibitors of an activated blood coagulation factor X. Compositions which contain, as an active ingredient, an FXa selective low-molecular weight FXa inhibitor having a short serum half-life are particularly useful as anticoagulants for an extracorporeal blood circuit.

23 Claims, 2 Drawing Sheets

U.S. PATENT DOCUMENTS

| | | | |
|---|---|---|---|
| 7,396,844 B1 * | 7/2008 | Takayanagi et al. | 514/359 |
| 7,402,568 B2 * | 7/2008 | Or et al. | 514/29 |
| 2001/0056123 A1 | 12/2001 | Nakagawa et al. | 514/619 |
| 2002/0055522 A1 | 5/2002 | Liebeschuetz et al. | 514/619 |
| 2002/0107290 A1 | 8/2002 | Nakagawa et al. | 514/619 |

FOREIGN PATENT DOCUMENTS

| | | |
|---|---|---|
| EP | 1 086 946 A1 | 3/2001 |
| EP | 1 236 735 | 9/2002 |
| JP | 11-140040 | 5/1999 |
| WO | WO 96/16940 A1 | 6/1996 |
| WO | WO 98/31661 A1 | 7/1998 |
| WO | WO 99/10316 A1 | 3/1999 |
| WO | WO 99/47503 A1 | 9/1999 |
| WO | WO 99/52895 A1 | 10/1999 |
| WO | WO 99/64392 A1 | 12/1999 |
| WO | WO 00/59876 A1 | 10/2000 |
| WO | WO 01/42254 A1 | 6/2001 |
| WO | 01/56989 | 8/2001 |
| WO | WO 01/74791 A1 | 10/2001 |
| WO | WO 02/26732 A1 | 4/2002 |
| WO | WO 02/28827 A1 | 4/2002 |
| WO | WO 02/42270 A1 | 5/2002 |
| WO | WO 03/080603 A1 | 10/2003 |
| WO | WO 2004/056813 A1 | 7/2004 |

OTHER PUBLICATIONS

Office Action issued Aug. 16, 2011, in Japanese Patent Application No. 501682/2007 (with English Translation).

* cited by examiner

BENZAMIDINE COMPOUND

CROSS REFERENCES TO RELATED APPLICATIONS

This application is a continuation of International Patent Application No. PCT/JP2006/2302202, filed on Feb. 2, 2006, and claims priority to Japanese Patent Application No. 2005-026949 filed on Feb. 2, 2005, both of which are incorporated herein by reference in their entireties.

BACKGROUND OF THE INVENTION

1. Field of the Invention

The present invention relates to novel benzamidine compounds which exhibit an activated blood coagulation factor X (hereinafter sometimes to be abbreviated as FXa) inhibitory activity. The present invention also related to a method of producing such compounds, intermediates useful for producing such compounds, and uses of such a benzamidine compound. The present invention also relates to a low-molecular weight FXa inhibitor, particularly the use of a low-molecular weight FXa inhibitor having a short half-life in blood, for an extracorporeal blood circuit and the like.

2. Discussion of the Background

Extracorporeal blood circulation is an artificial blood circulation through a blood circuit constructed outside the body. Generally, by the extracorporeal blood circulation, the blood is circulated in a circuit from a body via an extracorporeal artificial blood flow tube to an apparatus for a given treatment, for example, an artificial heart lung apparatus, blood purifying device and the like, and then into the body. An extracorporeal blood circulation treatment is sometimes required during a blood purification therapy such as hemodialysis, blood filtration, hemodialysis filtration, plasma exchange, and the like, a heart-lung bypass during open-heart operation and the like. As the blood purification device, a dialyzer and the like are typically mentioned.

When the blood is in contact with a foreign substance, the intrinsic blood coagulation cascade is generally activated, and the blood is finally coagulated and loses flowability. An extracorporeal blood circuit consisting of artificial blood flow tubes and various apparatuses, which is used for extracorporeal blood circulation is a foreign substance, and the blood coagulates upon contact therewith. Therefore, a treatment to prevent blood coagulation in the extracorporeal blood circuit by some means is needed.

Conventionally, anticoagulants such as unfractionated heparin, low-molecular-weight heparin and the like are used for the prevention of thrombus in the extracorporeal blood circuit.

However, unfractionated heparin cannot be used for patients with a high risk of bleeding since, it has a risk of creating a propensity toward hemorrhage due to its thrombin inhibitory activity in addition to the FXa inhibitory activity. Low-molecular-weight heparin is a pharmaceutical agent that inhibits FXa more selectively as compared to thrombin by a chemical treatment of heparin, and is free of a thrombin inhibitory activity. Thus, low-molecular-weight heparin shows a low tendency of causing bleeding, and has been used for patients having a tendency of bleeding. On the other hand, however, since low-molecular-weight heparin has a long disappearance half-life, hemostasis is difficult when the bleeding symptom is observed.

Furthermore, some serine protease inhibitors also have an anticoagulant action. For example, nafamostat mesilate is used for some extracorporeal blood circulations such as hemodialysis and the like. Since nafamostat mesilate has a short disappearance half-life in the body, it is also used for patients with a bleeding lesion. However, nafamostat mesilate does not have a strong inhibitory activity against FXa and thrombin, and shows a weak anticoagulant effect.

As mentioned above, all the pharmaceutical agents have problems yet to be solved, and there is a demand for a more effective and safe pharmaceutical agent.

Patients with an extracorporeal circuit face the problem of blood coagulation only when the circuit is used. Thus, the situation often varies from that of patients requiring continuous prevention of blood coagulation. It has not been assumed heretofore that a selective low-molecular weight FXa inhibitor with a short half-life in blood can be used safely and conveniently as an anticoagulant for the prevention of blood coagulation in an extracorporeal blood circuit, and that the treatment of and attention to hemostasis necessary after the completion of the extracorporeal blood circulation can be clearly reduced.

As a benzamidine compound that exhibits an anticoagulation activity based on a selective FXa inhibitory action, the compounds described in WO98/31661 and WO99/64392 are known. However, these compounds are clearly structurally different from the compound of the present invention which contain an ester structure in the molecular main chain.

SUMMARY OF THE INVENTION

Accordingly, it is one object of the present invention to provide novel benzamidine compounds and pharmaceutically acceptable salts thereof.

It is another object of the present invention to provide novel benzamidine compounds and pharmaceutically acceptable salts thereof which inhibit activated blood coagulation factor X.

It is another object of the present invention to provide novel methods of producing such a benzamidine compound or pharmaceutically acceptable salt thereof.

It is another object of the present invention to provide novel intermediates which are useful for preparing such a benzamidine compound or pharmaceutically acceptable salt thereof.

It is another object of the present invention to provide novel activated blood coagulation factor X inhibitors, which comprise such a benzamidine compound or pharmaceutically acceptable salt thereof.

It is another object of the present invention to provide novel anticoagulants, which comprise such a benzamidine compound or pharmaceutically acceptable salt thereof.

It is another object of the present invention to provide novel pharmaceutical compositions which contain such a benzamidine compound or pharmaceutically acceptable salt thereof.

It is another object of the present invention to provide novel anticoagulants and pharmaceutical compositions for an extracorporeal blood circuit.

It is another object of the present invention to provide novel methods of preventing thrombus formation in an extracorporeal blood circuit.

These and other objects, which will become apparent during the following detailed description, have been achieved by the inventors' discovery that particular novel benzamidine derivatives having an ester bond in the molecule, which is represented by

wherein A' and B' are organic groups, and at least one of them containing an amidino group or guanidino group structure, have a superior activated blood coagulation factor X inhibitory activity and a short half-life in blood, and are useful as blood anticoagulants for the extracorporeal blood circuit.

Accordingly, the present invention provides the following:

(1) A compound represented by the formula (1):

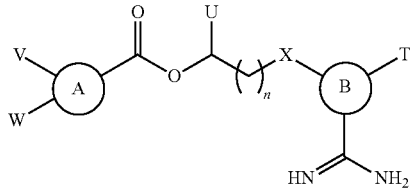

wherein, in formula (1), ring A and ring B are the same or different and each is a $C_{6-10}$ aryl group, a $C_{1-10}$ heteroaryl group, a $C_{2-8}$ nitrogen-containing non-aromatic heterocyclic group or a $C_{3-10}$ cycloalkyl group;

T is a hydrogen atom, a hydroxyl group, a $C_{1-10}$ alkoxy group optionally having substituent(s), a $C_{1-10}$ acyloxy group optionally having substituent(s), a carbamoyloxy group optionally having substituent(s), a thiocarbamoyloxy group optionally having substituent(s), an amino group, a halogen atom, a cyano group, a nitro group, a $C_{1-10}$ alkyl group optionally having substituent(s), a $C_{1-10}$ alkylamino group optionally having substituent(s), a $C_{1-10}$ alkylthio group optionally having substituent(s), a $C_{1-10}$ acylamino group optionally having substituent(s), a carboxyl group, a $C_{2-10}$ alkoxycarbonyl group optionally having substituent(s), a carbamoyl group optionally having substituent(s), or a thiocarbamoyl group optionally having substituent(s);

U is a hydrogen atom, a $C_{1-10}$ alkyl group optionally having substituent(s), a carboxyl group, a $C_{2-10}$ alkoxycarbonyl group optionally having substituent(s), or a carbamoyl group optionally having substituent(s);

V is a hydrogen atom, a halogen atom, a hydroxyl group, a $C_{1-10}$ alkyl group optionally having substituent(s), a $C_{1-10}$ alkoxy group optionally having substituent(s), a $C_{1-10}$ alkylamino group optionally having substituent(s), a $C_{1-10}$ allylthio group optionally having substituent(s), a cyano group, a nitro group, a carboxyl group, or a carbamoyl group optionally having substituent(s);

W is a $C_{1-10}$ heteroaryl group, or a group represented by the following formula (2-1), (2-2) or (2-3),

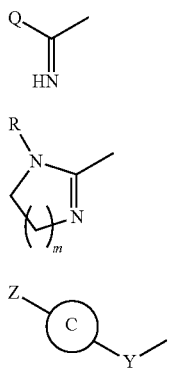

wherein in the formula (2-1),

Q is a $C_{1-6}$ alkyl group, an amino group optionally substituted by $C_{1-10}$ alkyl group(s), or a $C_{2-8}$ nitrogen-containing heterocyclic group having a bond at the nitrogen atom;

in the formula (2-2),

R is a $C_{1-6}$ alkyl group, and m is an integer of 1-3; and in the formula (2-3), ring C is a $C_{2-8}$ nitrogen-containing heterocyclic group, Y is a nitrogen atom optionally substituted by a $C_{1-6}$ alkyl group, an oxygen atom, a sulfur atom, or a methylene group; and Z is a hydrogen atom, an amidino group optionally substituted by $C_{1-6}$ alkyl group(s), or a $C_{1-6}$ alkyl group optionally having an imino group at the 1-position;

X is a nitrogen atom optionally substituted by a $C_{1-6}$ alkyl group, an oxygen atom, a sulfur atom, or a methylene group; and n is an integer of 1-3, or a pharmaceutically acceptable salt thereof.

(2) The compound of the above-mentioned (1), which is represented by the following formula (1-2):

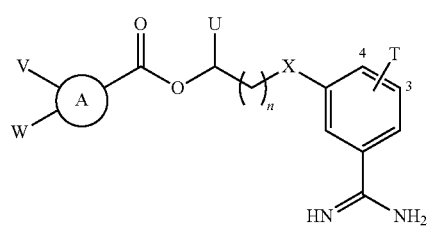

wherein ring A, T, U, V, W, X, and n are defined as the above-mentioned (1); and T substitutes the benzamidine at the 3-position or the 4-position, or a pharmaceutically acceptable salt thereof.

(3) The compound of the above-mentioned (2), wherein, in the formula (1-2),

X is an oxygen atom or a sulfur atom;

U is a hydrogen atom or a $C_{1-6}$ alkyl group;

T is a hydrogen atom, a hydroxyl group, a $C_{1-10}$ alkoxy group optionally having substituent(s), a $C_{2-10}$ acyloxy group optionally having substituent(s), a carbamoyloxy group optionally having substituent(s), or a thiocarbamoyloxy group optionally having substituent(s); and n is arm integer of 1-2, or a pharmaceutically acceptable salt thereof.

(4) The compound of the above-mentioned (3), wherein, in the formula (1-2), ring A is a phenyl group, a pyridyl group, a thiophenyl group, a piperidinyl group, or a piperazinyl group; and V is a hydrogen atom, a halogen atom, or a $C_{1-6}$ alkyl group, or a pharmaceutically acceptable salt thereof.

(5) The compound of the above-mentioned (4), wherein, in the formula (1-2),

W is a pyridyl group, or a group represented by the formula (2-1), (2-2) or (2-3), in the formula (2-1);

Q is an amino group, a $C_{1-10}$ alkylamino group, or a $C_{2-8}$ nitrogen-containing heterocyclic group having a bond at the nitrogen atom;

in the formula (2-3), ring C is a $C_{2-8}$ nitrogen-containing heterocyclic group;

Y is an oxygen atom, a sulfur atom, or a methylene group; and

Z is a hydrogen atom, an amidino group, or a $C_{1-6}$ alkyl group optionally having an imino group at the 1-position, or a pharmaceutically acceptable salt thereof.

(6) A pharmaceutical composition comprising a compound of any of the above-mentioned (1) to (5) or a pharmaceutically acceptable salt thereof.

(7) The pharmaceutical composition of the above-mentioned (6), which is an activated blood coagulation factor X inhibitor.

(8) The pharmaceutical composition of the above-mentioned (6), which is an anticoagulant.

(9) Tire pharmaceutical composition of the above-mentioned (8), which is an anticoagulant for an extracorporeal blood circuit in use.

(10) The pharmaceutical composition of the above-mentioned (9), wherein the extracorporeal blood circuit is used for hemodialysis.

(11) A method of inhibiting an activated blood coagulation factor X, which comprises administering an effective amount of a compound of any of the above-mentioned (1) to (5) or a pharmaceutically acceptable salt thereof to a subject in need thereof.

(12) Use of the compound of any of the above-mentioned (1) to (5) or a pharmaceutically acceptable salt thereof for the production of an activated blood coagulation factor X inhibitor.

(13) A method for anticoagulation, which comprises applying the compound of any of the above-mentioned (1) to (5) or a pharmaceutically acceptable salt thereof.

(14) Use of the compound of any of the above-mentioned (1) to (5) or a pharmaceutically acceptable salt thereof for the production of an anticoagulant.

(15) A dialysate or a dialysate concentrate comprising the compound of any of the above-mentioned (1) to (5) or a pharmaceutically acceptable salt thereof.

(16) in anticoagulant for an extracorporeal blood circuit comprising low-molecular weight FXa inhibitor as an active ingredient.

(17) The anticoagulant for an extracorporeal blood circuit of the above-mentioned (16), wherein the low-molecular weight FXa inhibitor is rapidly cleared from the blood.

(18) The anticoagulant for an extracorporeal blood circuit of the above-mentioned (17), wherein the low-molecular weight FXa inhibitor is FXa selective.

(19) The method for anticoagulation, which encompasses application of a low-molecular weight FXa inhibitor.

(20) The method for anticoagulation of the above-mentioned (19), which is used for an extracorporeal blood circuit.

(21) Use of a low-molecular weight FXa inhibitor for the production of an anticoagulant.

(22) Use of the above-mentioned (21) for the production of an anticoagulant to be applied to an extracorporeal blood circuit.

(23) A commercial package comprising a low-molecular weight FXa inhibitor, and a written instruction regarding the low-molecular weight FXa inhibitor, which indicates that the low-molecular weight FXa inhibitor can be used or should be used as an anticoagulant.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1B, Example 20 administration group (5 mg/hour); and FIG. 1C, Example 20 administration group (15 mg/hour), N=5).

DETAILED DESCRIPTION OF THE PREFERRED EMBODIMENTS

Figure 1:
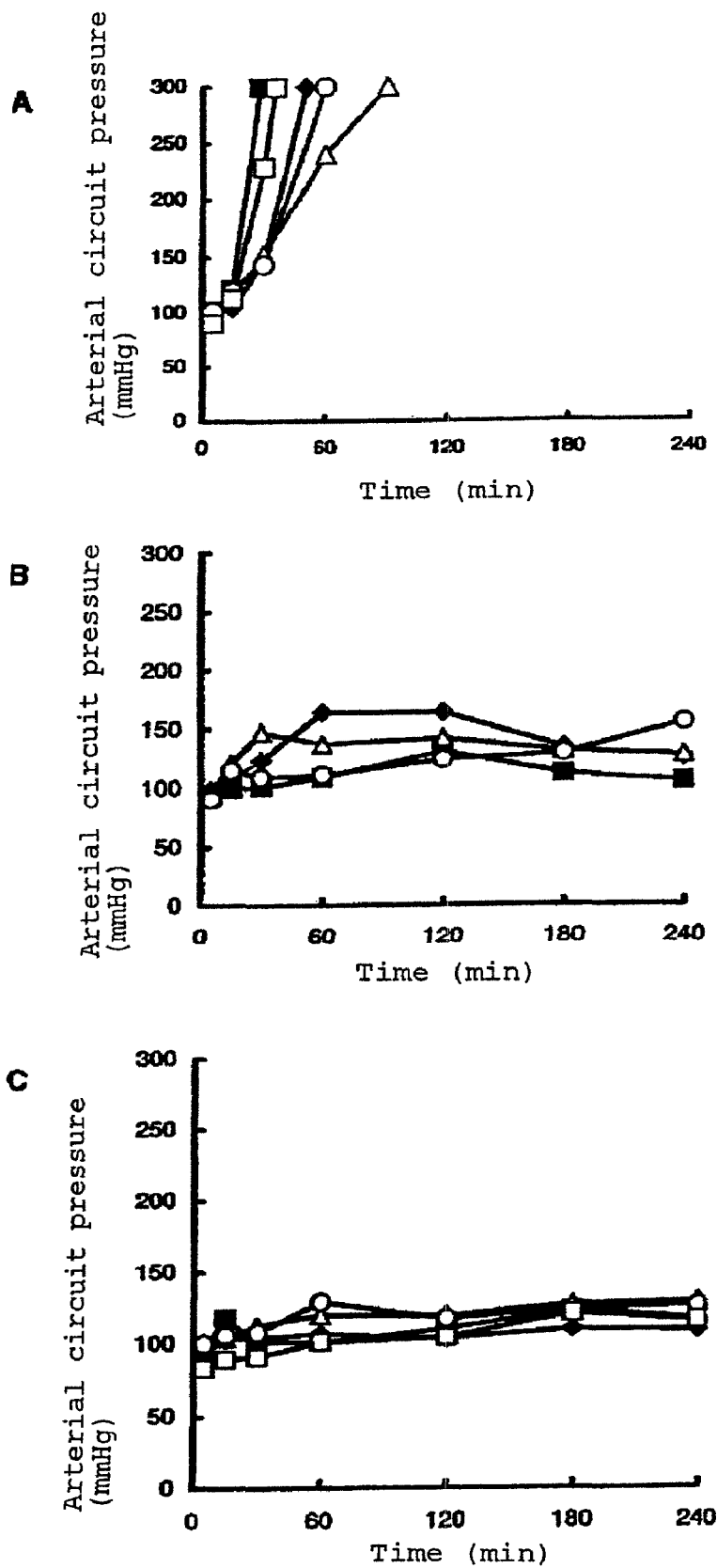
FIG. 1 shows the time course changes of the arterial circuit pressure in dog dialysis models (FIG. 1A, saline administration group.

The terms to be used in the present specification are defined as follows.

The term aryl group refers to an optionally substituted monocyclic-bicyclic aromatic hydrocarbon ring group, or phenyl group to which a 5- to 8-membered cycloalkyl ring (e.g., cyclopentane ring, cyclohexane ring, cycloheptane ring, cyclooctane ring, etc.) has been condensed. For example, phenyl group, naphthyl group, indanyl group, and tetrahydronaphthalenyl group can be mentioned. Generally, the aryl group has 6-14 carbon atoms, and $C_{6-10}$ aryl groups are preferable. Phenyl group and naphthyl group are more preferable, and a phenyl group is particularly preferable.

The term heteroaryl group refers to a 5- to 10-membered monocyclic-bicyclic aromatic hetero ring group containing, as ring atom, 1 to 6 hetero atoms selected from oxygen atom, sulfur atom, and nitrogen atom, which optionally has substituent(s). As examples of the aromatic hetero rings encompassed in the heteroaryl group, for example, pyridine ring, pyridazine ring, pyrimidine ring, pyrazine ring, furan ring, thiophene ring, pyrrole ring, isoxazole ring, oxazole ring, isothiazole ring, thiazole ring, pyrazole ring, imidazole ring, oxadiazole ring, thiadiazole ring, triazole ring, tetrazole ring, benzofuran ring, benzothiophene ring, indole ring, isoindole ring, benzoxazole ring, benzothiazole ring, benzimidazole ring (=benzoimidazole ring), indazole ring, benzisoxazole ring, benzisothiazole ring, benzofurazan ring, benzothiadiazol ring, purine ring, quinoline ring, isoquinoline ring, cinnoline ring, phthalazine ring, quinazoline ring, quinoxaline ring, pteridine ring, imidazooxazole ring, imidazothiazole ring, imidazoimidazole ring, and the like can be mentioned. Generally, a heteroaryl group having 1-10 carbon atoms is preferable, a $C_{1-9}$ heteroaryl group is more preferable. Pyridine ring, pyridazine ring, pyrimidine ring, pyrazine ring, furan ring, thiophene ring, pyrrole ring, isoxazole ring, oxazole ring, isothiazole ring, thiazole ring, pyrazole ring, imidazole ring, oxadiazol ring, thiadiazol ring, triazole ring and tetrazole ring are further preferable, and pyridine ring and thiophene ring are particularly preferable.

The term non-aromatic heterocyclic group (i.e., aliphatic heterocyclic group) refers to a 4- to 12-membered monocyclic-bicyclic non-aromatic heterocyclic group containing, as ring atom, 1 to 4 hetero atoms selected from oxygen atom, sulfur atom and nitrogen atom. Preferably, the group has 1 to 9 carbon atoms. Furthermore, any of the carbon atoms as ring atoms may be substituted by oxo group(s), and the ring may include double bond(s) or triple bond(s). Moreover, the ring may be condensed with benzene ring optionally having substituent(s). As the non-aromatic heterocycle, for example, pyrrolidine ring, pyrazolidine ring, imidazolidine ring, pyrroline ring, pyrazoline ring, imidazoline ring, tetrahydrofuran ring, tetrahydrothiophene ring, tetrahydroquinoline ring, tetrahydroisoquinoline ring, thiazolidine ring, piperidine ring, piperazine ring, quinuclidine ring, tetrahydropyran ring, morpholine ring, thiomorpholine ring, dioxolane ring, homopiperidine ring, homopiperazine ring, indoline ring, isoindoline ring, chroman ring, isochroman ring and the like can be mentioned. Preferably $C_{2-8}$ non-aromatic heterocycle, more preferably pyrrolidine ring, pyrroline ring, tetrahydrofuran ring, tetrahydrothiophene ring, piperidine ring, piperazine ring, morpholine ring, thiomorpholine ring, homopiperidine ring and homopiperazine ring, particularly preferably pyrrolidine ring, piperidine ring, and homopiperidine ring can be mentioned.

The term nitrogen-containing non-aromatic heterocyclic group (i.e., nitrogen-containing aliphatic heterocyclic group) refers to the above-mentioned non-aromatic heterocyclic group containing nitrogen atom(s) in the ring. As the nitrogen-containing non-aromatic heterocycle, pyrrolidine ring, piperidine ring, homopiperidine ring, piperazine ring, tetrahydroquinoline ring, tetrahydroisoquinoline ring, and pyrroline ring are preferable. Generally those having 1-9 carbon atoms, preferably those having 2-9 carbon atoms can be mentioned, a nitrogen-containing non-aromatic heterocyclic group having 2 to 8 (carbon atoms is more preferable, and pyrrolidine ring, piperidine ring, and piperazine are particularly preferable.

The term cycloalkyl group refers to an aliphatic hydrocarbon ring group, and the group may contain double bond(s) in its ring. As the aliphatic hydrocarbon ring, for example, cyclpropane ring, cyclobutane ring, cyclopentane ring, cyclohexane ring, cycloheptane ring, cyclooctane ring, cyclohexene ring, cyclopentene ring, and the like can be mentioned. Preferably, a $C_{3-10}$ cycloalkyl group can be mentioned, and more preferably cyclohexane ring can be mentioned.

The alkyl group moiety for alkyl group, or alkylthio group, alkylamino group, alkoxy group, alkoxycarbonyl group, and the like, is a straight chain, branched chain, cyclic or partially cyclic alkyl group. For example, methyl group, ethyl group, propyl group, isopropyl group, butyl group, isobutyl group, sec-butyl group, tert-butyl group, cyclopropylmethyl group, pentyl group, isopentyl group, neopentyl group, hexyl group, heptyl group, octyl group, nonyl group, decyl group, 1,1-dimethyl-propyl group, cyclopropyl group, cyclobutyl group, cyclopentyl group, cyclohexyl group, cycloheptyl group, cyclooctyl group, and the like can be mentioned. A $C_{1-10}$ alkyl group is preferable, a $C_{1-6}$ alkyl group is more preferable, methyl group, ethyl group, isopropyl group, isobutyl group and cyclopropyl group are more preferable, and a $C_{1-3}$ alkyl group is particularly preferable. Methyl group, ethyl group, isopropyl group, and cyclopropyl group are still more preferable.

Examples of the $C_{1-10}$ alkylthio group include methylthio group, ethylthio group, propylthio group, isopropylthio group, butylthio group, isobutylthio group, sec-butylthio group, tert-butylthio group, cyclopropylmethylthio group, pentylthio group, isopentylthio group, neopentylthio group, hexylthio group, heptylthio group, octylthio group, nonylthio group, decylthio group, 1,1-dimethyl-propylthio group, cyclopropylthio group, cyclobutylthio group, cyclopentylthio group, cyclohexylthio group, cycloheptylthio group, cyclooctylthio group, and the like.

Examples of the $C_{1-10}$ alkylamino group include methylamino group, ethylamino group, propylamino group, isopropylamino group, butylamino group, isobutylamino group, sec-butylamino group, tert-butylamino group, cyclopropylmethylamino group, pentylamino group, isopentylamino group, neopentylamino group, hexylamino group, heptylamino group, octylamino group, nonylamino group, decylamino group, 1,1-dimethyl-propylamino group, cyclopropylamino group, cyclobutylamino group, cyclopentylamino group, cyclohexylamino group, cycloheptylamino group, cyclooctylamino group; dimethylamino group, diethylamino group, dipropylamino group, diisopropylamino group, dibutylamino group, diisobutylamino group, di-sec-butylamino group, di-tert-butylamino group, di(cyclopropylmethyl) amino group, dipentylamino group, diisopentylamino group, dineopentylamino group, dihexylamino group; N-methyl-N-ethylamino group, N-methyl-N-propylamino group, N-methyl-N-isopropylamino group, N-methyl-N-butylamino group, N-methyl-N-isobutylamino group, N-methyl-N-sec-butylamino group, N-methyl-N-tert-butylamino group, N-ethyl-N-propylamino group, N-ethyl-N-isopropylamino group, N-ethyl-N-butylamino group, N-ethyl-N-isobutylamino group, N-ethyl-N-sec-butylamino group, N-ethyl-N-tert-butylamino group, and the like.

Examples of the $C_{1-10}$ alkoxy group include methoxy group, ethoxy group, propoxy group, isopropoxy group, butoxy group, isobutoxy group, sec-butoxy group, tert-butoxy group, cyclopropylmethoxy group, pentyloxy group, isopentyloxy group, neopentyloxy group, hexyloxy group, heptyloxy group, octyloxy group, nonyloxy group, decyloxy group, 1,1-dimethyl-propoxy group, cyclopropoxy group, cyclobutoxy group, cyclopentyloxy group, cyclohexyloxy group, cycloheptyloxy group, cyclooctyloxy group, and the like.

Examples of the $C_{2-10}$ alkoxycarbonyl group include methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, cyclopropylmethoxycarbonyl group, pentyloxycarbonyl group, isopentyloxycarbonyl group, neopentyloxycarbonyl group, hexyloxycarbonyl group, heptyloxycarbonyl group, octyloxycarbonyl group, nonyloxycarbonyl group, 1,1-dimethyl-propoxycarbonyl group, cyclopropoxycarbonyl group, cyclobutoxycarbonyl group, cyclopentyloxycarbonyl group, cyclohexyloxycarbonyl group, cycloheptyloxycarbonyl group, cyclooctyloxycarbonyl group, and the like.

As the acyl group as the component of acyl group, or acyloxy group, acylamino group, and the like, a $C_{1-11}$ acyl group such as formyl group, a $C_{2-10}$ alkylcarbonyl group (e.g., acetyl group, ethylcarbonyl group, propylcarbonyl group, isopropylcarbonyl group, butylcarbonyl group, isobutylcarbonyl group, sec-butylcarbonyl group, tert-butylcarbonyl group, cyclopropylmethylcarbonyl group, pentylcarbonyl group, isopentylcarbonyl group, neopentylcarbonyl group, hexylcarbonyl group, heptylcarbonyl group, octylcarbonyl group, nonylcarbonyl group, 1,1-dimethyl-propylcarbonyl group, cyclopropylcarbonyl group, cyclobutylcarbonyl group, cyclopentylcarbonyl group, cyclohexylcarbonyl group, cycloheptylcarbonyl group, cyclooctylcarbonyl group, etc.), a $C_{2-11}$ arylcarbonyl group (e.g., benzoyl group, 1-naphthylcarbonyl group, 2-naphthylcarbonyl group, etc.), and the like can be mentioned. Of these, a $C_{1-10}$ acyl group is preferable, and a $C_{1-7}$ acyl group is more preferable. Particularly, a $C_{1-6}$ acyl group is preferable.

Examples of the $C_{1-11}$ acyloxy group include formyloxy group, $C_{2-10}$ alkylcarbonyloxy group (e.g., acetyloxy group, ethylcarbonyloxy group, propylcarbonyloxy group, isopropylcarbonyloxy group, butylcarbonyloxy group, isobutylcarbonyloxy group, sec-butylcarbonyloxy group, tert-butylcarbonyloxy group, cyclopropylmethylcarbonyloxy group, pentylcarbonyloxy group, isopentylcarbonyloxy group, neopentylcarbonyloxy group, hexylcarbonyloxy group, heptylcarbonyloxy group, octylcarbonyloxy group, nonylcarbonyloxy group, 1,1-dimethyl-propylcarbonyloxy group, cyclopropylcarbonyloxy group, cyclobutylcarbonyloxy group, cyclopentylcarbonyloxy group, cyclohexylcarbonyloxy group, cycloheptylcarbonyloxy group, cyclooctylcarbonyloxy group, etc.), a $C_{2-11}$ arylcarbonyloxy group (e.g., benzoyloxy group, etc.), and the like. A $C_{1-10}$ acyloxy group is preferable, and a $C_{1-7}$ acyloxy group is more preferable.

Examples of the $C_{1-11}$ acylamino group include formylamino group, a $C_{2-10}$ alkylcarbonylamino group (e.g., acetylamino group, ethylcarbonylamino group, propylcarbonylamino group, isopropylcarbonylamino group, butylcarbonylamino group, isobutylcarbonylamino group, sec-butylcarbonylamino group, tert-butylcarbonylamino group, cyclopropylmethylcarbonylamino group, pentylcarbonylamino group, isopentylcarbonylamino group, neopentylcarbonylamino group, hexylcarbonylamino group, heptylcarbonylamino group, octylcarbonylamino group, nonylcarbonylamino group, 1,1-dimethyl-propylcarbonylamino group, cyclopropylcarbonylamino group, cyclobutylcarbonylamino group, cyclopentylcarbonylamino group, cyclohexylcarbonylamino group, cycloheptylcarbonylamino group, cyclooctylcarbonylamino group, etc.), a $C_{2-11}$ arylcarbonylamino group (e.g., benzoylamino group, etc.) and the like. A $C_{1-10}$ acylamino group is preferable, and a $C_{1-7}$ acylamino group is more preferable.

The term nitrogen-containing heterocyclic group refers to the above-mentioned nitrogen-containing non-aromatic heterocyclic group, and the above-mentioned heteroaryl group containing nitrogen atom(s) in the ring, and a $C_{2-8}$ nitrogen-containing heterocyclic group is preferable; pyrrolidinyl group, piperidinyl group, homopiperidinyl group, morpholinyl group, thiomorpholinyl group, piperazinyl group, pyrrolinyl group, imidazolyl group, pyridyl group, and pyrrolyl group are more preferable; and pyrrolidinyl group, piperidinyl group, morpholinyl group, thiomorpholinyl group, and piperazinyl group are more preferable.

The term halogen atom refers to fluoro atom, chloro atom, bromo atom, and iodo atom. Preferably, fluoro atom and chloro atom can be mentioned.

The alkylamino group, or the alkylamino moiety as a component for the carbamoyl or thiocarbamoyl substituted by alkyl group(s) (cases where the substituent is alkyl group(s) in carbamoyl group, thiocarbamoyl group, carbamoyloxy group, thiocarbamoyloxy group, and the like, each of which optionally having substituent(s)), and the like, encompasses both monoalkylamino groups and dialkylamino groups. In the dialkylamino groups, the alkyl group may bond to form a ring (e.g., nitrogen-containing heterocycle in the above-mentioned nitrogen-containing heterocyclic group, etc.).

In the present specification, examples of the substituent for "optionally having substituent(s)" include, for example,
(1) halogen atom,
(2) hydroxyl group,
(3) amino group,
(4) $C_{1-10}$ alkyl group, preferably $C_{1-6}$ alkyl group,
(5) $C_{2-10}$ alkenyl group, preferably $C_{2-6}$ alkenyl group (e.g., vinyl group, allyl group, isopropenyl group, 1-butenyl group, 2-butenyl group, 3-butenyl group, butadienyl group, 2-methylallyl group, hexatrienyl group, 3-octenyl group, etc.),
(6) $C_{2-10}$ alkynyl group, preferably $C_{2-6}$ alkynyl group (e.g., ethynyl group, 2-propynyl group, isopropynyl group, butynyl group, tert-butynyl group, 3-hexynyl group, etc.),
(7) $C_{1-10}$ alkoxy group, preferably $C_{1-6}$ alkoxy group,
(8) $C_{1-10}$ alkylamino group, preferably $C_{1-6}$ alkylamino group,
(9) cyano group,
(10) guanidino group,
(11) carboxyl group,
(12) carbamoyl group,
(13) $C_{6-14}$ aryl group, preferably $C_{6-10}$ aryl group,
(14) $C_{1-10}$ heteroaryl group, preferably $C_{1-9}$ heteroaryl group,
(15) $C_{3-10}$ cycloalkyl group, preferably $C_{3-8}$ cycloalkyl group,
(16) nitrogen-containing non-aromatic heterocyclic group having 1-9 carbon atoms, preferably $C_{2-8}$ nitrogen-containing non-aromatic heterocyclic group,
(17) $C_{1-10}$ alkylthio group, preferably $C_{1-6}$ alkylthio group,
(18) $C_{1-10}$ acyloxy group, preferably $C_{1-6}$ acyloxy group,
(19) $C_{1-10}$ acylamino group, preferably $C_{1-6}$ acylamino group,
(20) $C_{1-10}$ alkylsulfonamide group, preferably $C_{1-6}$ alkylsulfonamide group (e.g., methylsulfonamide group, ethylsulfonamide group, propylsulfonamide group, isopropylsulfonamide group, butylsulfonamide group, isobutylsulfonamide group, sec-butylsulfonamide group, tert-butylsulfonamide group, cyclopropylmethylsulfonamide group, pentylsulfonamide group, isopentylsulfonamide group, neopentylsulfonamide group, hexylsulfonamide group, heptylsulfonamide group, octylsulfonamide group, nonylsulfonamide group, decylsulfonamide group, 1,1-dimethyl-propylsulfonamide group, cyclopropylsulfonamide group, cyclobutylsulfonamide group, cyclopentylsulfonamide group, cyclohaxylsulfonamide group, cycloheptylsulfonamide group, cyclooctylsulfonamide group, etc.),
(21) $C_{2-10}$ alkoxycarbonyl group, preferably $C_{2-7}$ alkoxycarbonyl group, and the like can be mentioned.

As the substituent, preferably,
(1) halogen atom,
(2) hydroxyl group,
(3) amino group,
(4) $C_{1-6}$ alkyl group,
(5) $C_{2-6}$ alkenyl group,
(6) $C_{2-6}$ alkynyl group,
(7) $C_{1-6}$ alkoxy group,
(8) $C_{1-6}$ alkylamino group,
(9) cyano group,
(10) guanidin) group,
(11) carboxyl group,
(12) carbamoyl group,
(13) $C_{1-6}$ acylamino group,
(14) $C_{3-8}$ cycloalkyl group,
(15) $C_{1-6}$ alkylthio group,
(16) $C_{1-10}$ acyloxy group, more preferably $C_{1-6}$ acyloxy group,
(17) $C_{1-6}$ alkylsulfonamide group and
(18) $C_{2-10}$ alkoxycarbonyl group,
can be mentioned.

The number and position of the substituent are not particularly limited.

The compound represented by the formula (1) of the present invention (hereinafter sometimes to be abbreviated to compound (1)) also encompasses various steric isomers such as geometric isomers, tautomers, optical isomers, and the like, and mixtures and isolated forms thereof.

In the above-mentioned formula (1),
as a group represented by ring A, phenyl group, naphthyl group, thienyl group, pyridyl group, piperidinyl group, and tetrahydroisoquinolyl group are preferable. Of these, phenyl group is particularly preferable.

The positions of the substituents V and W and the carbonyl group on ring A are not specifically limited so long they are substitutable positions on ring A.

As V, hydrogen atom is preferable.

As W, imino(pyrrolidin-1-yl)methyl group, (1-(1-iminoethyl)piperidin-4-yl)oxy group, and {1-aminopiperidin-4-yl}oxy group are preferable.

As the group represented by ring B, phenyl group, thienyl group, pyridyl group, pyrimidyl group, pyridazinyl group, pyrazyl group, and piperidinyl group are preferable. Of these, phenyl group and piperidinyl group are particularly preferable.

The positions of the substituents T and X and the amidino group on ring B are not specifically limited so long they are substitutable positions on ring B.

As T, hydrogen atom, hydroxyl group, methoxy group, ethoxy group, propoxy group, isobutoxy group, 2-hydroxyethoxy group, cyanomethoxy group, carboxymethoxy group, 2-cyanoethyl group, 2-carboxyethyl group, dimethylthiocarbamoyl group, cyclopropylmethoxy group, 1-pyrrolidinylethoxy group, aminoethyl group, acetylaminoethyl group, acyloxy group, dimethylcarbamoyl group, and 1-pyrrolidinylcarbonyl group are preferable. Hydrogen atom, hydroxyl group, methoxy group, ethoxy group, propoxy group, isobutoxy group, 2-hydroxyethoxy group, cyanomethoxy group, carboxymethoxy group, 2-cyanoethyl group, and 2-carboxyethyl group are more preferable. Of these, hydroxyl group, 2-hydroxyethoxy group and cyanomethoxy group are particularly preferable. Although the substitutable position of T on ring B is not particularly limited, where ring, B is 6-membered ring group, the substitutable position of T is the 3- or 4-position, preferably the 4-position, when substitutable position of the amidino group in the formula (1) is the 1-position.

As U, hydrogen atom and methyl group are preferable.

As V, hydrogen atom, fluoro atom, chloro atom, methoxy group, benzyloxy group and hydroxyl group are preferable, and hydrogen atom is particularly preferable.

W is $C_{1-10}$ heteroaryl group, or a group represented by the following formula (2-1), (2-2) or (2-3).

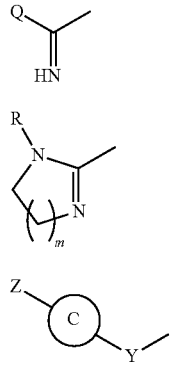

wherein each symbol is as defined in the present specification.

As W, 4-pyridyl group, amidino group, 1-iminoethyl group, imino(pyrrolidin-1-yl)methyl group, and imino(pyrroline-1-yl)methyl group can be preferably mentioned, and particularly preferably, imino(pyrrolidin-1-yl)methyl group can be mentioned.

In the formula (2-1),

Q is $C_{1-6}$ alkyl group, amino group optionally substituted by $C_{1-10}$ alkyl group (which may be either mono- or di-substituted (see the above-mentioned "$C_{1-10}$ alkylamino group")), or $C_{2-8}$ nitrogen-containing heterocyclic group having a bond at the nitrogen atom.

Examples of the $C_{1-6}$ alkyl group include methyl group, ethyl group, propyl group, isopropyl group, butyl group, isobutyl group, sec-butyl group, tert-butyl group, cyclopropylmethyl group, pentyl group, isopentyl group, neopentyl group, hexyl group, 1,1-dimethyl-propyl group, cyclopropyl group, cyclobutyl group, cyclopentyl group, and cyclohexyl group. Furthermore, examples of the $C_{2-8}$ nitrogen-containing heterocyclic group include pyrrolidinyl group, piperidinyl group, homopiperidinyl group, morpholinyl group, thiomorpholinyl group, piperazinyl group, imidazolinyl group, pyrrolinyl group, pyridyl group, and pyrrolyl group. As Q, 1-pyrrolidinyl group and 1-pyrrolinyl group are preferable. As the group represented by the formula (2-1), imino(pyrrolidin-1-yl)methyl group is preferable.

In the formula (2-2), R is $C_{1-6}$ alkyl group, and m is an integer of 1-3.

Examples of the $C_{1-6}$ alkyl group include methyl group, ethyl group, propyl group, isopropyl group, butyl group, isobutyl group, sec-butyl group, tert-butyl group, cyclopropylmethyl group, pentyl group, isopentyl group, neopentyl group, hexyl group, 1,1-dimethyl-propyl group, cyclopropyl group, cyclobutyl group, cyclopentyl group, and cyclohexyl group.

In the formula (2-2), R is preferably methyl group, and m is preferably 1. As the group represented by the formula (2-2), 1-methyl-4,5-dihydro-1H-imidazol-2-yl group is preferable.

In the formula (2-3), ring C is $C_{2-8}$ nitrogen-containing heterocyclic group, and examples of the nitrogen-containing heterocyclic group include pyrrolidinyl group, piperidinyl group, homopiperidinyl group, morpholinyl group, thiomorpholinyl group, piperazinyl group, imidazolinyl group, pyrrolinyl group, pyridyl group, and pyrrolyl group, and preferable examples include pyrrolidinyl group, piperidyl group, and homopiperidyl group. Of these, piperidyl group is particularly preferable.

Y is any of nitrogen atom optionally substituted by $C_{1-6}$ alkyl group (i.e., nitrogen atom substituted by $C_{1-6}$ alkyl group or —NH—), oxygen atom (—O—), sulfur atom (—S—), and methylene group (—CH$_2$—). As the $C_{1-6}$ alkyl group as the substituent, methyl group, ethyl group, propyl group, isopropyl group, butyl group, isobutyl group, sec-butyl group, tert-butyl group, cyclopropylmethyl group, pentyl group, isopentyl group, neopentyl group, hexyl group, 1,1-dimethyl-propyl group, cyclopropyl group, cyclobutyl group, cyclopentyl group, and cyclohexyl group can be mentioned. As Y, oxygen atom is preferable.

Z is hydrogen atom, amidino group optionally substituted by $C_{1-6}$ alkyl group, or $C_{1-6}$ alkyl group optionally having imino group at the 1-position. For Z, as the $C_{1-6}$ alkyl group, methyl group, ethyl group, propyl group, isopropyl group, butyl group, isobutyl group, sec-butyl group, tert-butyl group, cyclopropylmethyl group, pentyl group, isopentyl group, neopentyl group, hexyl group, 1,1-dimethyl-propyl group, cyclopropyl group, cyclobutyl group, cyclopentyl group, and cyclohexyl group can be mentioned. As Z, amidino group and 1-iminoethyl group are preferable.

As the group represented by the formula (2-3), 1-(1-iminoethyl)-4-piperidinyloxy group or 1-amidino-4-piperidinyloxy group is preferable.

The positions of the substituents Z and Y on ring C are not particularly limited so long as they are substitutable positions on ring C.

In the formula (1),

X is any of nitrogen atom optionally substituted by $C_{1-6}$ alkyl group (i.e., nitrogen atom substituted by $C_{1-6}$ alkyl group and —NH—), oxygen atom (—O—), sulfur atom (—S—) or methylene group (—CH$_2$—). As X, nitrogen atom (—NH—), oxygen atom (—O—) and sulfur atom (—S—) are preferable, oxygen atom and sulfur atom are more preferable, and oxygen atom is particularly preferable.

n is an integer of 1-3, preferably 1 or 2, and more preferably 1.

In the present invention, compounds having combinations of the preferable groups represented by the above-mentioned symbols are preferable.

More specifically, a compound represented by the following formula (1-2) is preferable.

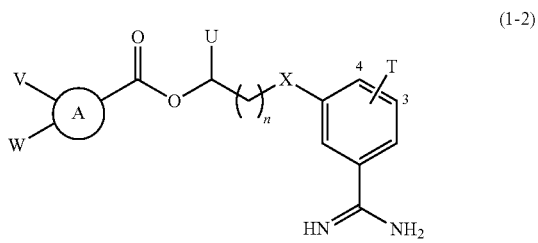

(1-2)

wherein ring A, T, U, V, W, X and n are as defined in the above-mentioned formula (1), and the 3- or 4-position on the benzamidine is substituted by T.

In the formula (1-2), as W-A(V)—, 4-[imino(pyrrolidin-1-yl)methyl]-phenyl group, 4-(1-(1-iminoethyl)-4-piperidinyloxy)phenyl group, and 4-(1-amidino-4-piperidinyloxy)phenyl group are preferable.

T is preferably hydrogen atom, 2-hydroxyethoxy group, methoxy group, cyanomethoxy group, hydroxyl group, 2-methylpropoxy group (isobutoxy group), or acetyloxy group, and as the substitutable position, the 4-position is preferable.

As X, oxygen atom and sulfur atom are preferable, and oxygen atom is more preferable, n is preferably 1, and U is preferably hydrogen atom or $C_{1-6}$ alkyl group, and more preferably hydrogen atom, methyl group, or ethyl group.

Furthermore, a compound of the formula (1-2), wherein

X is oxygen atom or sulfur atom,

U is hydrogen atom or $C_{1-6}$ alkyl group,

T is hydrogen atom, hydroxyl group, $C_{1-10}$ alkoxy group optionally having substituent(s), $C_{2-10}$ acyloxy group optionally having substituent(s), carbamoyloxy group optionally having substituent(s), or thiocarbamoyloxy group optionally having substituent(s), and n is an integer of 1-2 is more preferable.

In this case, a compound wherein ring A is phenyl group, pyridyl group, thiophenyl group, piperidinyl group, or piperazinyl group, and V is hydrogen atom, halogen atom, or $C_{1-6}$ alkyl group is more preferable.

Moreover, a compound wherein

W is any of pyridyl group, or a group represented by the formula (2-1), (2-2), or (2-3), wherein in the formula (2-1), Q is amino group, $C_{1-10}$ alkylamino group, or $C_{2-8}$ nitrogen-containing heterocyclic group having a bond at the nitrogen atom, and in the formula (2-3), ring C is any of $C_{2-8}$ nitrogen-containing heterocyclic group, and Y is oxygen atom, sulfur atom and methylene group, and Z is hydrogen atom, amidino group, or $C_{1-6}$ alkyl group optionally having imino group at the 1-position, is more preferable.

More specifically, the compounds described in Examples, but are not limited thereto, are preferable.

The present invention also relates to an anticoagulant for use in an extracorporeal blood circuit containing a low-molecular weight FXa inhibitor as an active ingredient and a method for preventing formation of thrombus in an extracorporeal blood circuit, which method comprises incorporating a low-molecular weight FXa inhibitor as a component of the circuit. In the present specification, the "low-molecular weight FXa inhibitor" refers to the above-mentioned compound represented by the formula (1) and a pharmaceutically acceptable salt thereof, or a compound having a molecular weight of not more than 1000, which has FXa inhibitory activity, preferably the compound represented by the formula (1). More specifically, as the compound having a molecular weight of not more than 1000, which has FXa inhibitory activity, for example, the compounds disclosed in WO99/52895, WO99/10316, WO2000/59876, WO2002/28827, WO01/74791, WO96/16940, and WO2002/42270, all of which are incorporated herein by reference, can be mentioned.

Furthermore, as the above-mentioned low-molecular weight FXa inhibitor, one that disappears quickly in the blood is preferable. In the present specification, the phrase "disappears quickly in the blood" means that the disappearance half-life in vivo or the half-life measured in the stability test in the plasma shown in the below-mentioned Experimental Example 4 is from 0.5 minutes to 10 minutes, preferably from 0.5 minutes to 5 minutes. Moreover, as the above-mentioned low-molecular weight FXa inhibitor, those which are FXa selective are preferable, more specifically those having a difference between $pIC_{50}$(FXa) and $pIC_{50}$(IIa), i.e., $pIC_{50}$(FXa)–$pIC_{50}$(IIa), of not less than 2.5 in the system for evaluating inhibitory activity shown in the below-mentioned Experimental Examples 1 and 2.

The term extracorporeal blood circulation refers to artificial blood circulation via a blood circuit constituted outside of a living organism, and the extracorporeal blood circuit refers to a blood circuit used for the extracorporeal blood circulation. Examples include a blood circuit made by connecting a living organism and an artificial organ when utilizing an artificial organ, and more specifically, for example, those used during use of an artificial heart-lung machine and during hemodialysis can be mentioned. In the present invention, an extracorporeal blood circuit used during hemodialysis is particularly preferable.

The representative production methods of the compounds represented by the formula (1) of the present invention (hereinafter sometimes to be abbreviated as compound (1)) are explained below. However, those of ordinary skill in the art will understand that the present invention is not limited by the following production methods.

In the formula (1), when ring A is an aryl group or heteroaryl group and W is a group represented by the formula (2-1) or (2-2), the intermediate (4) and intermediate (5) can be obtained in the method shown below. Specifically, for example, a cyanoarylcarboxylic acid such as 4-cyanobenzoic acid and the like or a cyanoheteroaiylcarboxylic acid is dissolved in a solvent, for example, an alcohol: $R^1OH$ (wherein $R^1$ is an alkyl group) such as methanol, ethanol and the like, and an acid, for example, hydrogen chloride gas, is blown into the mixture, whereby imidate (3) can be obtained. The obtained imidate (3) is reacted with, for example, an ammonium salt or a primary or secondary amine: $R^2R^3NH$ (wherein $R^2$ and $R^3$ are each the same or different and each is hydrogen atom or alkyl group, or $R^2$ and $R^3$ may form, together with the nitrogen atom to which they are bonded, to form $C_{2-8}$ nitrogen-containing heterocyclic group), such as ammonia, ammonium carbonate or the like, in a solvent, for example, an alcohol such as methanol, ethanol and the like, whereby amidine derivative (4) wherein W is represented by the formula (2-1) in the formula (1) can be obtained. Alternatively, using a similar manner, cyclic amidine derivative (5) wherein W is represented by the formula (2-2) in the formula (1) can be obtained by reacting imidate (3) with, for example, a diaminoalkane: R⁴—NH—CH₂—(CH₂)ₘ—NH₂ (wherein R⁴ is alkyl group, and m is an integer of 1-3) such as N-methylethylenediamine and the like.

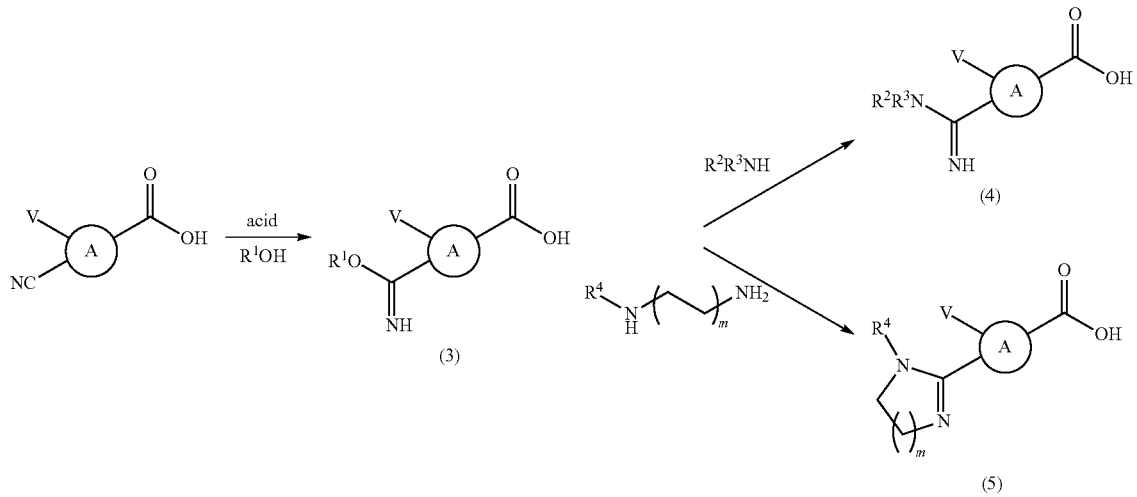

wherein each symbol is as defined above.

In the Formula (1), when ring A is nitrogen-containing non-aromatic heterocyclic group and W is amidino group optionally having substituent(s) (e.g., $C_{1-10}$ alkyl group, etc.) or 1-imino-alkyl group (e.g., 1-iminoethyl group), intermediate (6) can be obtained by the following method. That is, for example, a nitrogen-containing non-aromatic heterocycle carboxylic acid ester such as ethyl isonipecotate and the like can be dissolved in a solvent, for example, an alcohol such as methanol, ethanol, and the like in the presence of a base, for example, an organic base such as diisopropylethylamine, reacted with, for example, ethyl acetimidate or 1H-pyrazole-1-carboxamidine, whereby intermediate (6) can be obtained.

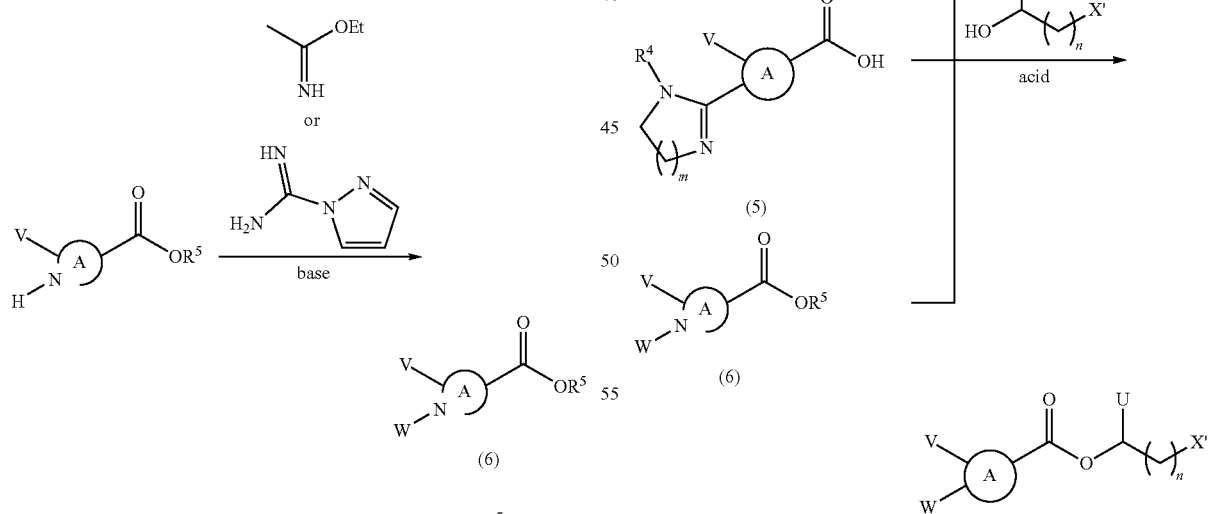

wherein each symbol is as defined above, and $R^5$ is alkyl group.

The thus-obtained intermediates (4), (5), and (6) can be each converted to intermediate (7) in the following methods. Specifically, intermediate (4), (5), or (6), is mixed, without any solvent, for example, with a halogeno alcohol: HO—CH(U)—(CH₂)ₙ—X' (wherein U and n are as defined above, X' is a leaving group such as halogen atom (e.g., fluorine atom, chlorine atom, bromine atom, iodine atom, etc.) and the like) such as 2-bromoethanol, 3-bromopropanol, and the like, a catalytic amount of organic acid, for example, an inorganic acid such as hydrochloric acid, sulfuric acid, and the like, or an organic acid such as p-toluenesulfonic acid, methanesulfonic acid, and the like is added to the mixture, and the mixture is heated, whereby intermediate (7) can be obtained.

wherein each symbol is as defined above.

When ring A is aryl group or heteroaryl group, W is the group represented by the formula (2-3), and X is oxygen atom in the formula (1), intermediate (7) can be obtained by the method shown below. Specifically, for example, a nitrogen-containing heterocycle having a hydroxyl group and its nitrogen atom is protected by a suitable protecting group (Prot) that can be removed under acidic condition (e.g., tert-butoxycarbonyl group, etc.), such as N-tert-butoxycarbonyl-4-hydroxypiperidine and the like, and for example, an arylcarboxylate or heteroarylcarboxylate having hydroxyl group such as ethyl 4-hydroxybenzoate and the like are dissolved in a solvent such as THF and the like, and reacted with diethylazodicarboxylic acid (DEAD) and triphenylphosphine, whereby ether (8) (wherein $R^6$ is alkyl group) can be obtained. The thus-obtained ether (8), is mixed, without solvent, with, for example, a halogeno alcohol: HO—CH(U)—(CH$_2$)$_n$—X' (wherein U and n are as defined above and X' is a leaving group such as halogen atom (e.g., fluorine atom, chlorine atom, bromine atom, and iodine atom, etc.) such as 2-bromoethanol, 3-bromopropanol, and the like. A catalytic amount of acid, for example, an inorganic acid such as hydrochloric acid, sulfuric acid, and the like, or an organic acid such as p-toluenesulfonic acid, methanesulfonic acid, and the like is added to the mixture, and the mixture is heated to remove the protecting group (Prot) on the nitrogen atom, whereby halogenoalkyl ester (9) can be obtained. The thus-obtained halogenoalkyl ester (9) is dissolved in a solvent, for example, an alcohol such as methanol, ethanol, and the like, and in the presence of a base, for example, an organic base such as diisopropylethylamine, reacted with, for example, ethyl acetimidate or 1H-pyrazole-1-carboxamidine, whereby intermediate (7) can be obtained.

When T is hydrogen atom or halogen atom in the formula (1), intermediate compound (12) can be in synthesized in the following method. Specifically, for example, a cyanohydroxyaryl such as 3-cyanophenol and the like or cyanohydroxyheteroaryl is dissolved in a solvent, for example, an alcohol: $R^7OH$ (wherein $R^7$ is alkyl group) such as methanol, ethanol, and the like, and an acid, for example, hydrogen chloride gas is blown into the mixture, whereby imidate (10) can be obtained. The thus-obtained imidate (10) is reacted with all ammonium salt, for example, ammonia or ammonium carbonate, and the like, using a solvent, for example, methanol, ethanol, and the like, whereby amidine (11) can be obtained. The thus-obtained amidine (11) and the above-mentioned intermediate (7) are dissolved in a solvent, for example, dimethylformamide, and a base, for example, an inorganic base such as potassium carbonate, cesium carbonate, and the like is added to the mixture and the mixture is heated, whereby compound (12) wherein T is hydrogen atom or halogen atom can be obtained.

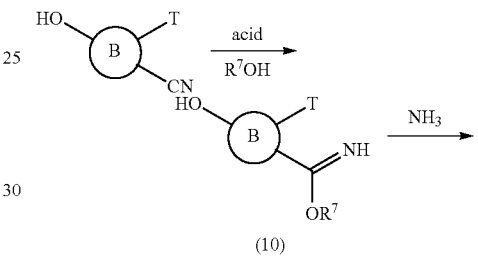

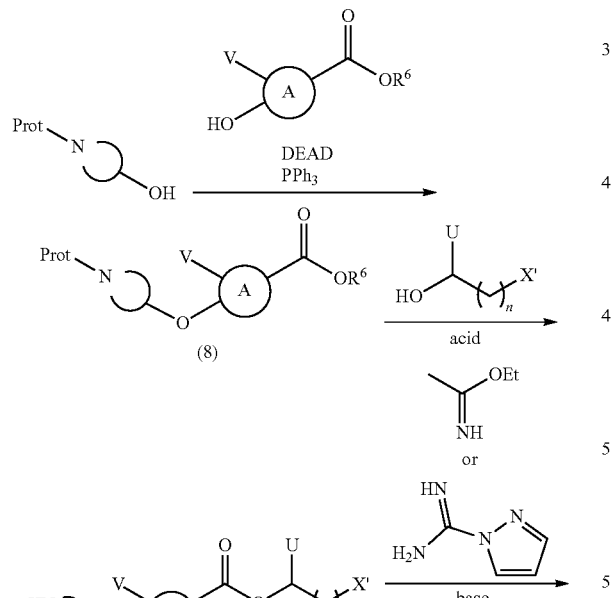

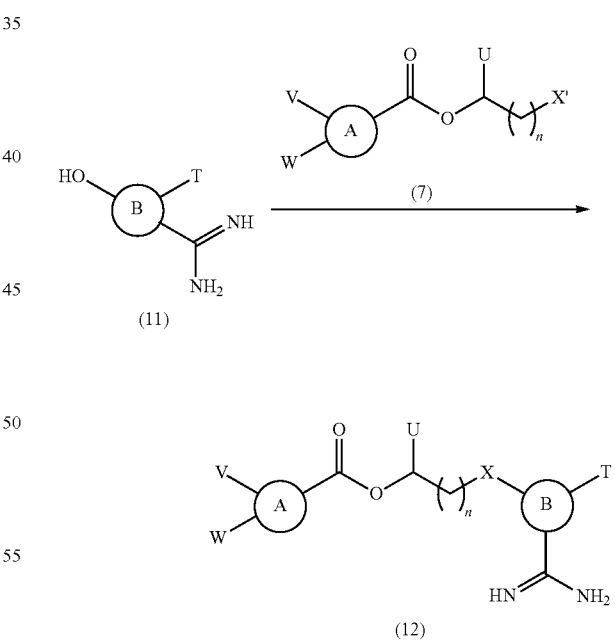

wherein each symbol is as defined above.

When T is attached to ring B via an oxygen atom such as hydroxyl group, alkoxy group optionally having substituent(s), acyloxy group optionally having substituent(s), carbamoyloxy group optionally having substituent(s) and the like in the formula (1), compound (17) can be synthesized by the following method.

Specifically, for example, a cyanodihydroxyaryl such as 3,4-dihydroxybenzonitrile and the like or a cyanodihydroxyheteroaryl is dissolved in a solvent such as dimethylformamide and reacted with benzyl halide: Bn-$X^a$ (wherein Bn is benzyl group and $X^a$ is halogen atom) and the like in the presence of a base, for example, an inorganic base such as potassium carbonate and heated, whereby nitrile (13) in which benzyl group is selectively attached to one hydroxyl group can be obtained. The thus-obtained nitrile (13) is dissolved in a solvent, for example, an alcohol: $R^8OH$ (wherein $R^8$ is alkyl group) such as methanol, ethanol, and the like, and an acid, for example, hydrogen chloride gas is blown into the mixture, whereby imidate (14) can be obtained. The thus-obtained imidate (14) is reacted with an ammonium salt such as ammonia or ammonium carbonate, and the like in a solvent, for example, an alcohol such as methanol, ethanol, and the like, whereby amidine (15) can be obtained. The thus-obtained amidine (15) and the above-mentioned intermediate (7) were dissolved in a solvent, for example, dimethylformamide, a base, for example, an inorganic base such as potassium carbonate, cesium carbonate, and the like is added to the mixture, and the mixture is heated, whereby intermediate (16) can be obtained. The thus-obtained intermediate (16) is dissolved in a solvent, for example, an alcohol such as methanol, ethanol, and the like or acetic acid, and subjected to catalytic reduction in the presence of a catalytic amount of palladium carbon, whereby compound (17) wherein T is hydroxyl, group can be obtained.

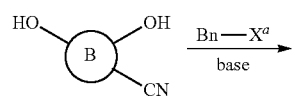

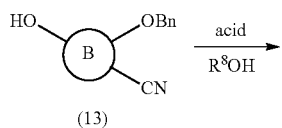

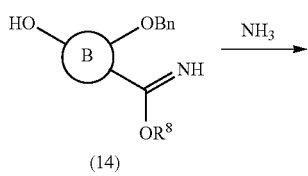

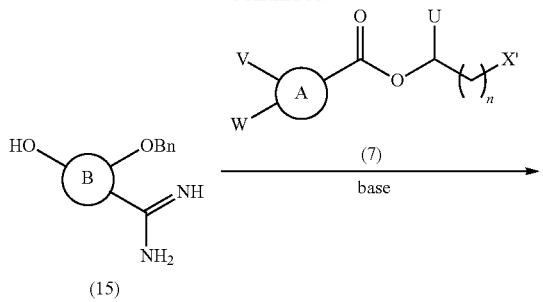

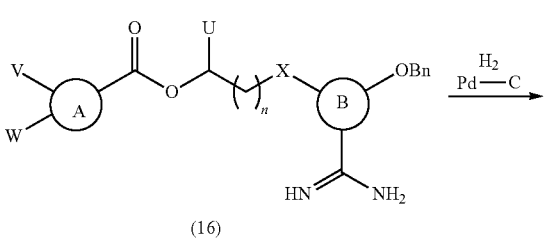

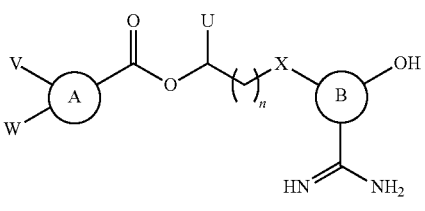

(17)

wherein each symbol is as defined above.

Furthermore, compound (17) wherein T is hydroxyl group is dissolved in a solvent, for example, dimethylformamide, and reacted with an alkyl halide: $X^b$—$R^9$ (wherein $X^b$ is a halogen atom, $R^9$ is an alkyl group optionally having substituent(s)), an acyl halide: $X^c$—CO—$R^{10}$ (wherein $X^c$ is a halogen atom, $R^{10}$ is alkyl group optionally having substituent(s) or aryl group optionally having substituent(s)), or a carbamoyl halide: $X^d$—CO—$NR^{11}R^{12}$ (wherein $X^d$ is a halogen atom, $R^{11}$ and $R^{12}$ are the same or different and each is hydrogen atom, or the "substituent" as defined above) in the presence of a base, for example, a inorganic base such as sodium hydrogencarbonate, potassium carbonate, cesium carbonate, and the like, whereby compound (18) wherein T is alkoxy group optionally having substituent(s), compound (19) wherein T is acyloxy group optionally having substituent(s), and compound (20) wherein T is carbamoyloxy group optionally having substituent(s) can be obtained, respectively.

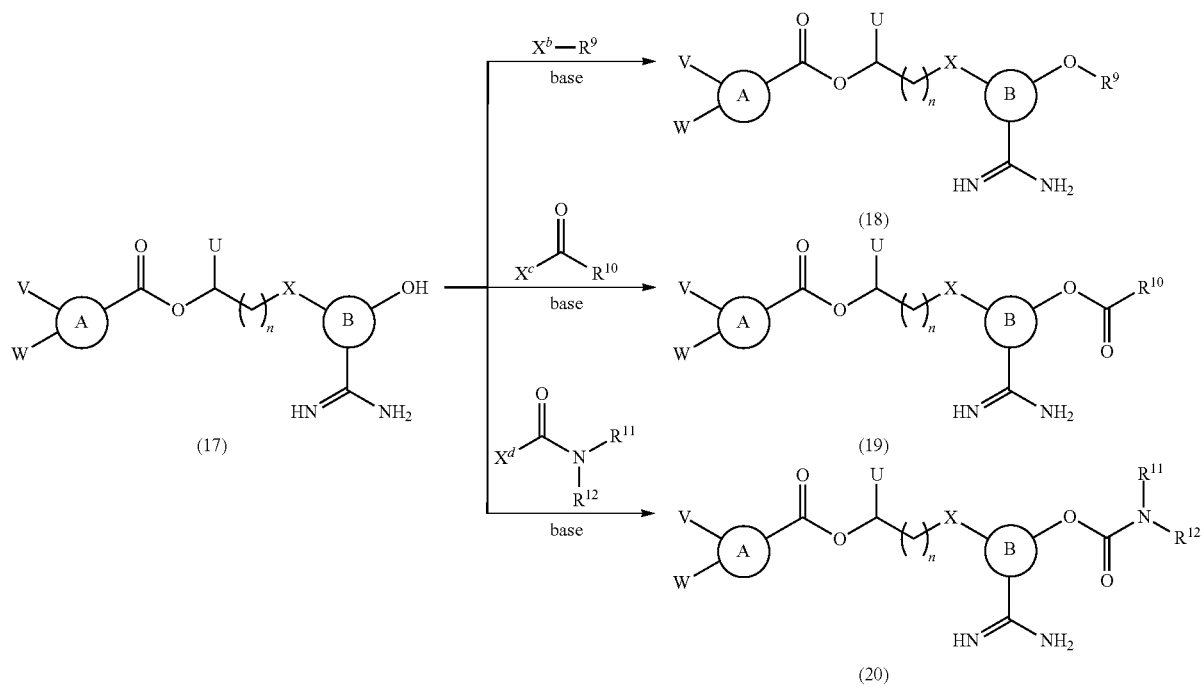

wherein each symbol is as defined above.

When the compound represented by the formula (1) of the present invention may form a salt, the salt may be a pharmaceutically acceptable salt, and examples in the case when an acidic group such as a carboxyl group and the like exists in the formula include an ammonium salt; a salt with an alkali metal such as sodium, potassium, and the like; a salt with an alkaline earth metal such as calcium, magnesium, and the like; an aluminum salt; a zinc salt; a salt with an organic amine such as triethylamine, ethanolamine, morpholine, piperidine, dicyclohexylamine, and the like; and a salt with a basic amino acid such as arginine, lysine and the like.

Examples of the salt in the case where a basic group exists in the formula include a salt with an inorganic acid such as hydrochloric acid, sulfuric acid, phosphoric acid, nitric acid, hydrogen bromide acid, and the like; a salt with an organic carboxylic acid such as acetic acid, trifluoroacetic acid (TFA), citric acid, benzoic acid, maleic acid, fumaric acid, tartaric acid, succinic acid, tannic acid, butyric acid, hibenzoic acid, pamoic acid, enanthic acid, decane acid, teoclic acid, salicylic acid, lactic acid, oxalic acid, mandelic acid, malic acid, and the like; and a salt with an organic sulfonic acid such as methanesulfonic acid, benzenesulfonic acid, p-toluenesulfonic acid, and the like. As the method of forming salts, mixing the compound of the formula (1) and a necessary acid or base in a suitable amount ratio in a solvent or a dispersing agent, or subjecting another salt form to cation exchange or anion exchange can be mentioned.

The compound of the present invention also encompasses solvates, for example, hydrates, alcoholates, and the like, of the compound represented by the formula (1).

The compound of the present invention can be prepared in the form of a prodrug. The prodrug in the present invention refers to a compound that is converted to the compound of the present invention in vivo. For example, when an active parent form comprises a carboxyl group or phosphoric acid group, examples of the prodrug include esters thereof, amides thereof, and the like. When an active parent form comprises an amino group, examples of the prodrug include amides thereof, carbamates thereof, and the like. When an active parent form comprises a hydroxyl group, examples of the prodrug include esters thereof, carbonates thereof, carbamates thereof, and the like. When the compound of the present invention is prepared in the form of a prodrug, the prodrug may be bonded to an amino acid or a saccharide.

The compound (1) of the present invention or a pharmaceutically acceptable salt thereof can be directly administered to a target or after formulation into a pharmaceutical composition by a conventional method using a conventional formulation aid. Examples of the dosage form for the pharmaceutical composition include tablets, powders, injections, freeze-dry injections, or, pills, granules, capsules, suppositories, liquids, sugar-coated agents, depots, syrups, suspensions, emulsions, troches, hypoglottis, patches, intraoral disintegrants (tablet), inhalants, enteroclysis, ointments, cloth adhesive agents, tapes, eye drops, and the like.

The compound or pharmaceutical composition of the present invention is administrated into a circuit for extracorporeal blood circulation or to a patient. Examples of preferable methods for the administration include direct administration into an extracorporeal blood circuit for circulation, intravenous administration, intramuscular administrations and subcutaneous administration. In some cases, oral administration, rectal administration, intranasal administrations or sublingual administration can be used. For direct administration into a circuit for extracorporeal blood circulation, the compound or pharmaceutical composition is preferably administered from a site of a circulation circuit drawing the blood from the body, which site is located as close as possible to the body. In the case of hemodialysis and the like, a generally installed injecting port can be utilized.

The administration subject is not particularly limited, and examples thereof include mammals (e.g., mouse, rat, hamster, rabbit, cat, dog, swine, bovine, sheep, horse, monkey, human, etc.) and the like.

In addition, as a manner of providing the compound of the present invention or a pharmaceutically acceptable salt thereof or a pharmaceutical composition comprising the compound or the salt as an anticoagulant for hemodialysis, for example, a manner wherein a FXa inhibitor composition is directly used in a dialyzer by dissolving or dispersing the composition in a dialysate prior to use, as well as a manner wherein the composition is provided in the form of a dialysate or a dialysate concentrate comprising a FXa inhibitor, may be mentioned. Examples of the dialysate concentrate include a powder preparation for an artificial kidney, which can be prepared, for example, by concentrating, a dialysate comprising a FXa inhibitor by freeze-drying and the like. The dialysate concentrate can be diluted prior to use, for example, with purified water by an appropriate method to afford a dialysate.

The compound or pharmaceutical composition of the present invention may be administered at once or continuously, in one portion or several portions as necessary, in one operation of extracorporeal blood circulation. The dose of the compound of the present invention or pharmaceutical composition may be from 0.01 mg to 10 g, preferably from 1 mg to 1,000 mg, as an active ingredient compound per one operation of extracorporeal blood circulation or per one day, which can be appropriately increased or decreased according to the age, body weight, symptom, and the like of the patient/target. While the appropriate concentration of the active ingredient compound in the dialysate depends on the compound to be used, severity of the disease to be treated and characteristic of the patient to be treated, the average concentration of the usable compound in the plasma at appropriate equilibrium generally includes a concentration within the range of from 0.0001 to 1000·mol/L, preferably from 0.005 to 20·mol/L.

The compound represented by the formula (1) and the pharmaceutically acceptable salt thereof can be utilized as a therapeutic or prophylactic drug for various diseases in which a FXa-dependent coagulation process is involved in the pathology. Examples of the disease include, besides the above-mentioned thrombus formation during extracorporeal blood circulation, cerebral infarction, cerebral thrombus, cerebral embolism, transient cerebral ischemic attack (TIA), acute and chronic myocardial infarction, unstable angina pectoris, pulmonary embolism, peripheral arterial occlusive disease, deep vein thrombosis, disseminated intravascular coagulation syndrome, thrombus formation after artificial vascular prosthesis or replacement of artificial valve, reocclusion and restenosis after coronary-artery bypass surgery, reocclusion and restenosis after reconstruction of blood vessel such as percutaneous transluminal coronary angioplasty (PTCA), percutaneous transluminal coronary recanaryzation (PTCR) and the like, and the like.

Other features of the invention will become apparent in the course of the following descriptions of exemplary embodiments which are given for illustration of the invention and are not intended to be limiting thereof.

EXAMPLES

Example 1

2-{3-amidinophenoxy}ethyl 1-pyridin-4-ylpiperidine-4-carboxylate ditrifluoroacetate Step 1. Synthesis of 2-(3-cyanophenoxy)ethyl acetate.

3-Cyanophenol (10.1 g, 84.8 mmol) and potassium carbonate (19.5 g, 141 mmol) were suspended in acetone (280 ml), 2-bromoethyl acetate (7.8 ml, 70.7 mmol) was added, and the mixture was stirred at 50° C. for 8 hours. Sodium iodide (1.06 g, 7.07 mmol) was added to the reaction mixture, and the mixture was heated under reflux for two nights and concentrated under reduced pressure. The residue was diluted with ethyl acetate, and the mixture was washed with 1N sodium hydroxide, 1N hydrochloric acid, and saturated brine, and dried over anhydrous sodium sulfate. The solvent was evaporated under reduced pressure to give the title compound without purification.

yield 8.94 g (43.6 mmol, 51%)
$^1$H-NMR (CDCl$_3$) δ 2.11 (3H, s), 4.20 (2H, br), 4.44 (2H, br), 7.14-7.16 (1H, m), 7.26-7.28 (1H, m), 7.36-7.41 (1H, m).

Step 2. Synthesis of 3-(2-hydroxyethoxy)benzonitrile.

2-(3-Cyanophenoxy)ethyl acetate (3.01 g, 14.7 mmol) obtained in Step 1 was dissolved in a mixed solvent of methanol and tetrahydrofuran (1:1), and 2N lithium hydroxide solution (14.7 ml) was added under ice-cooling. The mixture was stirred at room temperature for 45 min, 3N hydrochloric acid (10 ml) was added under ice-cooling, and the mixture was concentrated under reduced pressure. The residue was diluted with ethyl acetate, and the mixture was washed with 1N hydrochloric acid, saturated aqueous sodium hydrogencarbonate solution, and saturated brine, and dried over anhydrous sodium sulfate. The solvent was evaporated under reduced pressure. The obtained residue was purified by silica gel chromatography (hexane:ethyl acetate 85:15-55:45) to give the title compound.

yield 1.75 g (10.7 mmol, 73%)
$^1$H-NMR (CDCl$_3$) δ 3.98-4.01 (2H, m), 4.09-4.12 (2H, m), 7.15-7.18 (2H, m), 7.25-7.28 (1H, m), 7.36-7.42 (1H, m).

Step 3. Synthesis of tert-butyl[3-(2-hydroxyethoxy)phenyl](imino)methylcarbamate.

3-(2-Hydroxyethoxy)benzonitrile (1.60 g, 9.81 mmol) obtained in Step 2 was dissolved in anhydrous ethanol (570 μl) and 4N hydrochloric acid/1,4-dioxane solution (5.1 ml), and the mixture was stirred in a closed system at room temperature for two nights. The solvent was evaporated under reduced pressure, anhydrous ethanol (30 ml) and ammonium carbonate (4.7 g, 49 mmol) were added to the obtained residue, and the mixture was stirred at room temperature for 6 hours. The solvent was evaporated under reduced pressure, and the obtained residue was suspended in dimethylformamide (20 ml). Triethylamine (4.1 ml, 29.4 mmol) and a solution (10 ml) of di-tert-butyldicarbonate (4.28 g, 19.6 mmol) in dimethylformamide were added dropwise under ice-cooling, and the mixture was stirred at room temperature overnight. N,N-Dimethylethylenediamine (2.2 ml, 19.6 mmol) was added under ice-cooling, and the mixture was stirred at room temperature for 30 minutes and concentrated under reduced pressure. The residue was diluted with ethyl acetate, and the mixture was washed with saturated aqueous ammonium chloride solution, saturated aqueous sodium hydrogencarbonate solution, and saturated brine, and dried over anhydrous sodium sulfate. The organic layer was filtered through silica gel, and the solvent was evaporated under reduced pressure to give the title compound.

yield 64.5 mg (0.127 mmol, 37%)
MS (ESI, m/z) 281 (MH+)
$^1$H-NMR (CDCl$_3$) δ 1.55 (9H, s), 3.95 (2H, t), 4.13 (2H, t), 7.04-7.08 (1H, m), 7.30-7.36 (2H, m), 7.44-7.45 (1H, m).

Step 4. Synthesis of 2-{3-[[(tert-butoxycarbonyl)amino](imino)methyl]phenoxy}ethyl 1-pyridin-4-ylpiperidine-4-carboxylate.

1-Pyridin-4-ylpiperidine-4-carboxylic acid hydrochloride (573 mg, 2.36 mmol) was suspended in dichloromethane (15 ml), and oxalyl chloride (403 μl, 4.72 mmol) and a catalytic amount of DMF were added. The mixture was stirred at room temperature for 15 minutes and concentrated under reduced pressure, tetrahydrofuran (15 ml) and triethylamine (658 μl) were added to the residue, and tert-butyl[3-(2-hydroxyethoxy)phenyl](imino)methylcarbamate (440 mg, 1.57 mmol) obtained in Step 3 was added under ice-cooling. The mixture was stirred at room temperature for 30 minutes, and the solvent was evaporated under reduced pressure. The obtained residue was subjected to reversed-phase HPLC using, as a filler, silica gel to which octadodecyl group was chemically bonded, and eluted with a mixed solution of water and acetonitrile, which contains 0.1% trifluoroacetic acid (v/v), and the objective fraction was lyophilized to give the title compound.

yield 85.4 mg (0.147 mmol, 9.3%)
MS (ESI, m/z) 469 (MH+)

Step 5. Synthesis of 2-{3-amidinophenoxy}ethyl 1-pyridin-4-ylpiperidine-4-carboxylate ditrifluoroacetate.

2-{3-[[(tert-Butoxycarbonyl)amino](imino)methyl]phenoxy}ethyl 1-pyridin-4-ylpiperidine-4-carboxylate (85 mg, 0.147 mmol) obtained in Step 4 was dissolved in glacial acetic acid (2 ml), and trifluoroacetic acid (3 ml) was added thereto. The mixture was stirred at room temperature for 1.5 hours, and concentrated under reduced pressure, and the obtained residue was purified by reversed-phase HPLC in the same manner as in Step 4 to give the title compound.

yield 57.0 mg (0.0955 mmol, 65%)
MS (ESI, m/z) 369 (MH+)
$^1$H-NMR (DMSO-$d_6$) δ 1.56-1.70 (2H, m), 1.9.5-2.01 (2H, m), 2.85 (1H, sept), 3.28-3.37 (2H, m), 4.11-4.16 (2H, m), 4.31-4.32 (2H, m), 4.42-4.43 (2H, m), 7.19-7.22 (2H, m), 7.30-7.34 (1H, m), 7.42-7.44 (2H, m), 7.54 (1H, t), 8.24 (2H, d), 9.34 (2H, s), 9.57 (2H, s).

Example 2

2-{3-amidinophenoxy}ethyl 4-[imino(pyrrolidin-1-yl)methyl]benzoate ditrifluoroacetate Step 1. Synthesis of 3-hydroxybenzamidine trifluoroacetate.

To 3-cyanophenol (5.00 g, 42.0 mmol) were added anhydrous ethanol (6.1 ml, 210 mmol) and 4N hydrochloric acid/1,4-dioxane solution (55 ml), and the mixture was stirred in a closed system at room temperature for three nights. The solvent was evaporated under reduced pressure, and the obtained residue was added slowly at −78° C. to ethanol (210 ml) into which ammonia gas had been blown at the same temperature for 30 minutes. The temperature was gradually raised to room temperature, and the mixture was stirred overnight. The solvent was evaporated under reduced pressure, diethyl ether and ethanol were added to the residue, and the precipitated crystals (5.89 g) were collected by filtration. 2 g thereof was purified by reversed-phase HPLC in the same manner as in Step 4 of Example 1 to give the title compound.

yield 964 mg (3.85 mmol, 27%)
MS (ESI, m/z) 137 (MH+)
$^1$H-NMR (DMSO-$d_6$) δ 7.11-7.22 (3H, m), 7.41 (1H, t), 9.24 (4H, s).

Step 2. Synthesis of 4-[imino(pyrrolidin-1-yl)methyl]benzoic acid hydrochloride.

4-Cyanobenzoic acid (10.0 g, 68.0 mmol) was dissolved in anhydrous ethanol (10 ml) and 4N hydrochloric acid/1,4-dioxane 90 ml, and the mixture was stirred in a closed system at room temperature for two nights, and further stirred in an open system for at 35° C. 3 hours. The solvent was evaporated under reduced pressure, and the obtained residue was suspended in anhydrous ethanol (100 ml), and pyrrolidine (11.4 ml, 136 mmol) was added thereto, and the mixture was stirred at room temperature overnight. The precipitated crystals were collected by filtration, and washed with diethyl ether containing a small amount of 4N hydrochloric acid/1,4-dioxane, and the crystals were collected by filtration to give the title compound.

yield 5.56 g (25.5 mmol, 37%)
MS (ESI, m/z) 219 (MH+)
$^1$H-NMR (CD$_3$OD) δ 1.94-2.02 (2H, m), 2.14-2.23 (2H, m), 3.49 (2H, t), 3.63 (2H, t), 7.58 (2H, d), 8.08 (2H, d).

Step 3. Synthesis of 2-bromoethyl 4-[imino(pyrrolidin-1-yl)methyl]benzoate trifluoroacetate.

4-[Imino(pyrrolin-1-yl)methyl]benzoic acid hydrochloride (2.17 g, 8.52 mmol) obtained in Step 2 was dissolved in 2-bromoethanol (20 ml), p-toluenesulfonic acid monohydrate (162 mg, 0.852 mmol) was added thereto, and the mixture was stirred at 85° C. overnight. The solvent was evaporated under reduced pressure, and the obtained residue was purified by reversed-phase HPLC in the same manner as in Step 4 of Example 1 to give the title compound.

yield 3.39 g (7.72 mmol, 91%)
MS (ESI, m/z) 325 (MH+)
$^1$H-NMR (DMSO-$d_6$) δ 1.85 (2H, quint), 2.04 (21H, quint), 3.34 (2H, t), 3.54 (2H, t), 3.83 (2H, t), 4.63 (2H, t), 7.80 (2H, d), 8.15 (2H, d), 8.91 (1H, s), 9.37 (1H, d).

Step 4. Synthesis of 2-{3-amidinophenoxy}ethyl 4-[imino(pyrrolidin-1-yl)methyl]benzoate ditrifluoroacetate.

3-Hydroxybenzamidine trifluoroacetate (1.19 g, 6.92 mmol) obtained in Step 1, 2-bromoethyl 4-[imino(pyrrolidin-1-yl)methyl]benzoate trifluoroacetate (1.52 g, 3.46 mmol) obtained in Step 3, and cesium carbonate (4.51 g, 13.8 mmol) were stirred at 50° C. overnight in anhydrous N,N-dimethylformamide (35 ml). 3N hydrochloric acid (9 ml) was added under ice-cooling, the solvent was evaporated under reduced pressure, and the obtained residue was purified by reversed-phase HPLC in the same manner as in Step 4 of Example 1 to give the title compound.

yield 404 mg (0.664 mmol, 19%)
MS (ESI, m/z) 381 (MH+)
$^1$H-NMR (DMSO-$d_6$) δ 1.86 (2H, quint), 2.06 (2H, quint), 3.34 (2H, t), 3.56 (2H, t), 4.47 (2H, m), 4.71 (2H, m), 7.35-7.44 (3H, m), 7.79 (2H, d), 8.14 (2H, d), 8.94 (1H, s), 9.32 (4H, d), 9.39 (1H, s).

Example 3

2-{3-amidinophenoxy}ethyl 4-({N-methyl-N-[2-methylaminoethyl]-amino}carbonyl)benzoate ditrifluoroacetate Step 1. Synthesis of 2-{4-[(2-bromoethoxy)carbonyl]phenyl}-1,3-dimethyl-4,5-dihydro-1H-imidazo-3-lium trifluoroacetate.

4-Cyanobenzoic acid (10.1 g, 68.9 mmol) was dissolved in anhydrous ethanol (10 ml) and 4N hydrochloric acid/1,4-dioxane (100 ml), and the mixture was stirred in a closed system at room temperature for two nights. The solvent was evaporated under reduced pressure, and the obtained residue was suspended in anhydrous ethanol (50 ml). N,N'-Dimethylethylenediamine (7.4 ml, 68.9 mmol) was added, and the mixture was stirred at room temperature overnight. The solvent was evaporated under reduced pressure, and the obtained residue (500 mg, 1.77 mmol) was dissolved in 2-bromoethanol (3 ml). p-Toluenesulfonic acid monohydrate (5 mg) was added, and the mixture was stirred at 50° C. for 2 days. The temperature was raised to 70° C., and the mixture was further stirred overnight. The solvent was evaporated under reduced pressure, and the obtained residue was purified by reversed-phase HPLC in the same manner as in Step 4 of Example 1 to give the title compound.

yield 310 mg (0.706 mmol, 40%)
MS (ESI, m/z) 325 (MH+)

Step 2. Synthesis of 2-{3-amidinophenoxy}ethyl 4-({N-methyl-N-[2-methylaminoethyl]-amino}carbonyl)benzoate ditrifluoroacetate.

2-{4-[(2-Bromoethoxy)carbonyl]phenyl}-1,3-dimethyl-4,5-dihydro-1H-imidazo-3-lium trifluoroacetate (136 mg, 0.310 mmol) obtained in Step 1,3-hydroxybenzamidine trifluoroacetate (93 mg, 0.372 mmol) obtained in Step 1 of Example 2, and potassium carbonate (129 mg, 0.930 mmol) were suspended in N,N-dimethylformamide (3.5 ml), and the mixture was stirred at 50° C. for 2 hours. The solvent was evaporated under reduced pressure, and the obtained residue was purified by reversed-phase HPLC in the same manner as in Step 4 of Example 1 to give the title compound.

yield 40.4 mg (0.0644 mmol, 21%)
MS (ESI, m/z) 399 (MH+)
$^1$H-NMR (DMSO-d$_6$) δ 2.65 (3H, s), 2.89 (3H, s), 3.22 (2H, br), 3.76 (2H, br), 4.47 (2H, br), 4.68 (2H, br), 7.36-7.42 (1H, m), 7.45-7.46 (2H, m), 7.52-7.58 (1H, m), 7.63-7.66 (2H, m), 8.03 (2H, dd), 8.75 (2H, br), 9.33 (2H, s), 9.50 (2H, s).

Example 4

2-{3-amidinophenoxy}ethyl 4-methyl-1-pyridin-4-ylpiperidine-4-carboxylate ditrifluoroacetate Step 1. Synthesis of 1-tert-butyl 4-ethyl 4-methylpiperidine-1,4-dicarboxylate.

Ethyl N-tert-butoxycarbonyl isonipecotate (2.0 g, 7.8 mmol) was dissolved in THF (40 ml), and 2.0 M-THF solution (7.8 ml, 15.5 mmol) of lithium diisopropylamide was added dropwise at −78° C. After stirring for 10 minutes, iodomethane (1.21 ml, 19.4 mmol) was added, and the temperature was raised to 0° C. over 3 hours. The reaction was quenched with saturated aqueous ammonium chloride solution (10 ml), and the solvent was evaporated under reduced pressure. The residue was diluted with ethyl acetate, and the mixture was washed with 1N hydrochloric acid, 1N aqueous sodium hydroxide solution and saturated brine, the organic layer was dried over anhydrous magnesium sulfate, and concentrated under reduced pressure. The obtained residue was purified by the silica gel chromatography (hexane:ethyl acetate 100:0-1:4) to give the title compound.

yield 1.92 g (7.08 mmol, 91%)
$^1$H-NMR (CDCl$_3$) δ 1.13 (3H, s), 1.20 (3H, t), 1.40 (9H, s), 1.30 (2H, br t), 2.00 (2H, br d), 2.93 (2H, hr t), 3.71 (2H, br d), 4.11 (2H, q).

Step 2. Synthesis of ethyl 4-methyl-1-pyridin-4-ylpiperidine-4-carboxylate.

1-tert-Butyl 4-ethyl 4-methylpiperidine-1,4-dicarboxylate (500 mg, 1.84 mmol) obtained in Step 1 was dissolved in 4N hydrochloric acid/1,4-dioxane (4 ml), and the mixture was stirred at room temperature for 30 minutes. The solvent was evaporated under reduced pressure, and the obtained residue was dissolved in ethanol (18.4 ml). 4-Chloropyridine hydrochloride (276 mg, 1.84 mmol) and triethylamine (2.57 ml, 18.4 mmol) were added thereto, and the reaction mixture was stirred at 170° C. overnight in a sealed tube. The mixture was concentrated under reduced pressure, and the obtained residue was purified by silica gel chromatography (hexane:ethyl acetate 95:5-10:90) to give the title compound.

yield 198 mg (0.78 mmol, 43%)
MS (ESI, m/z) 249 (MH+)
$^1$H-NMR (CDCl$_3$) δ 1.24 (3H, s), 1.27 (3H, t), 1.51 (2H, ddd), 2.20 (2H, br d), 3.04 (2H, ddd), 3.61 (2H, ddd), 4.18 (2H, q), 6.64 (2H, d), 8.24 (2H, d).

Step 3. Synthesis of 4-methyl-1-pyridin-4-ylpiperidine-4-carboxylic acid trifluoroacetate.

Ethyl 4-methyl-1-pyridin-4-ylpiperidine-4-carboxylate (100 mg, 0.40 mmol) obtained in Step 2 was dissolved in methanol (1 ml), 1N lithium hydroxide aqueous solution (2.0 ml, 2.0 mmol) was added, and the mixture was stirred at room temperature for 2 hours. The reaction was quenched with 1N hydrochloric acid (4 ml), the solvent was evaporated under reduced pressure, and the obtained residue was purified by reversed-phase HPLC in the same manner as in Step 4 of Example 1 to give the title compound.

yield 115 mg (0.34 mmol, 86%)
MS (ESI, m/2) 221 (MH+)
$^1$H-NMR (DMSO-d$_6$) δ 1.20 (3H, s), 1.51 (2H, ddd), 2.20 (2H, br d), 3.04 (2H, ddd), 3.61 (2H, ddd), 7.20 (2H, d), 8.22 (2H, d).

Step 4. Synthesis of 2-{3-amidinophenoxy}ethyl 4-methyl-1-pyridin-4-ylpiperidine-4-carboxylate ditrifluoroacetate.

4-Methyl-1-pyridin-4-ylpiperidine-4-carboxylic acid trifluoroacetate (58 mg, 0.17 mmol) obtained in Step 3 was suspended in dichloromethane (1.5 ml), DMF (5 μL) and oxalyl chloride (148 μL, 0.86 mmol) were added, and the mixture was stirred for 15 minutes. The solvent was evaporated under reduced pressure, and the obtained residue was dissolved in dichloromethane (0.5 ml). A catalytic amount of DMAP and tert-butyl[3-(2-hydroxyethoxy)phenyl](imino)methylcarbamate (96 mg, 0.34 mmol) obtained in Step 3 of Example 1 were added thereto, and the mixture was stirred at room temperature for 10 minutes. Pyridine (20 μL) was added, and the mixture was stirred for 1 hour. Acetic acid (1 ml) and trifluoroacetic acid (2 ml) were added to the reaction mixture, and the mixture was stirred at room temperature for 1 hour. The solvent was evaporated under reduced pressure, and the obtained residue was purified by reversed-phase HPLC in the same manner as in Step 4 of Example 1 to give the title compound.

yield 4.1 mg (0.007 mmol, 4%)
MS (ESI, m/z) 383 (MH+)
$^1$H-NMR (DMSO-d$_6$) δ 1.21 (3H, s), 1.51 (2H, ddd), 2.10 (2H, br d), 3.34 (2H, ddd), 3.96 (2H, ddd), 4.49 (2H, br), 4.60 (2H, br), 7.20 (2H, d), 7.22-7.60 (4H, m), 8.22 (2H, d), 9.32 (4H, s).

Example 5

2-{3-amidinophenoxy}ethyl 4-(1-methyl-4,5-dihydro-1H-imidazol-2-yl)benzoate ditrifluoroacetate Step 1. Synthesis of 2-bromoethyl 4-(1-methyl-4,5-dihydro-1H-imidazol-2-yl)benzoate trifluoroacetate.

4-Cyanobenzoic acid (5.00 g, 34.0 mmol) was dissolved in anhydrous ethanol (3.9 ml) and 4N hydrochloric acid/1,4-dioxane (36 ml), and the mixture was stirred in a closed system at room temperature for three nights. The solvent was evaporated under reduced pressure, and the obtained residue (1.53 g) was suspended in anhydrous ethanol 25 ml. N-Methylethylenediamine (700 μl, 7.9 mmol) was added thereto, and the mixture was stirred at room temperature overnight. The reaction mixture was concentrated under reduced pressure, and the obtained residue was dissolved in 2-bromoethanol (7 ml). p-Toluenesulfonic acid monohydrate (about 10 mg) was added thereto, and the mixture was stirred at 70° C. overnight. p-Toluenesulfonic acid (10 mg) was added again, and the mixture was stirred at 70° C. overnight. The solvent was evaporated under reduced pressure, and the residue was purified by reversed-phase HPLC in the same manner as in Step 4 of Example 1 to give the title compound.

yield 360 mg (0.847 mmol, about 21%)
MS (ESI, m/z) 311 (MH+)

Step 2. Synthesis of 2-{3-amidinophenoxy}ethyl 4-(1-methyl-4,5-dihydro-1H-imidazol-2-yl)benzoate ditrifluoroacetate.

3-Hydroxybenzamidine trifluoroacetate (42 mg, 0.168 mmol) obtained in Step 1 of Example 2,2-bromoethyl 4-(1-methyl-4,5-dihydro-1H-imidazol-2-yl)benzoate trifluoroacetate (59.5 mg, 0.140 mmol) obtained in Step 1, and potassium carbonate (58.0 mg, 0.42 mmol) were suspended in N,N-dimethylformamide (1 ml), and the mixture was stirred at 50° C. for 6.5 hours. The reaction mixture was ice-cooled, 1N hydrochloric acid (840 μl) was added, and the mixture was sufficiently stirred, and concentrated under reduced pressure. The obtained residue was purified by reversed-phase HPLC in the same manner as in Step 4 of Example 1 to give the title compound.

yield 25.4 mg (0.0427 mmol, 31%)
MS (ESI, m/z) 367 (MH+)
$^1$H-NMR (DMSO-d$_6$) δ 3.04 (3H, s), 3.92-4.13 (4H, m), 4.48 (2H, br), 4.71 (2H, br), 7.30-7.58 (4H, m), 7.85 (2H, d), 8.18 (2H, d), 9.33 (2H, s), 9.43 (2H, s), 10.59 (1H, s).

Example 6

2-{5-amidino-2-hydroxyphenoxy}ethyl 4-[imino(pyrrolidin-1-yl)methyl]benzoate ditrifluoroacetate Step 1. Synthesis of 4-(benzyloxy)-3-hydroxybenzonitrile.

3,4-Dihydroxybenzonitrile (5.20 g, 38.5 mmol) and potassium carbonate (5.85 g, 42.4 mmol) were suspended in N,N-dimethylformamide (120 ml), benzyl bromide (4.58 ml) was added, and the mixture was stirred at 50° C. for 3 hours. The solvent was evaporated under reduced pressure, and the residue was diluted with ethyl acetate. The mixture was washed with 1N hydrochloric acid and saturated brine, dried over anhydrous magnesium sulfate, and concentrated under reduced pressure. The obtained residue was purified by silica gel chromatography (hexane:ethyl acetate 8:1-4:1) to give the title compound.

yield 6.02 g (26.8 mmol, 70%)
$^1$H-NMR (CDCl$_3$) δ 5.17 (2H, s), 5.91 (1H, s), 6.97 (1H, s), 7.16 (1H, d), 7.18 (1H, d), 7.41 (5H, s).

Step 2. Synthesis of 4-(benzyloxy)-3-hydroxybenzamidine trifluoroacetate.

4-(1-Benzyloxy)-3-hydroxybenzonitrile (4.35 g, 19.3 mmol) obtained in Step 1 was dissolved in anhydrous ethanol (3 ml) and 4N hydrochloric acid/1,4-dioxane solution (27 ml), and the mixture was stirred in a closed system at room temperature for two nights. The solvent was evaporated under reduced pressure, anhydrous ethanol (60 ml) and ammonium carbonate (9.27 g, 96.5 mmol) were added to the obtained residue, and the mixture was stirred at room temperature for 4 hours. The solvent was evaporated under reduced pressure, and the obtained residue was purified by reversed-phase HPLC in the same manner as in Step 4 of Example 1 to give the title compound.

yield 1.56 mg (6.42 mmol, 33%)
MS (ESI, m/z) 243 (MH+)
$^1$H-NMR (DMSO-d$_6$) δ 5.26 (2H, s), 7.18-7.26 (3H, m), 7.30-7.42 (3H, m), 7.48-7.50 (2H, m), 8.98 (2H, s), 9.05 (2H, s), 9.73 (1H, s).

Step 3. Synthesis of 2-{5-amidino-2-hydroxyphenoxy}ethyl 4-[imino(pyrrolidin-1-yl)methyl]benzoate ditrifluoroacetate.

4-(Benzyloxy)-3-hydroxybenzamidine trifluoroacetate (101 mg, 0.284 mmol) obtained in Step 2,2-bromoethyl 4-[imino(pyrrolidin-1-yl)methyl]benzoate trifluoroacetate (125 mg, 0.284 mmol) obtained in Step 3 of Example 2, and cesium carbonate (277 mg, 0.852 mmol) were suspended in anhydrous N,N-dimethylformamide, and the mixture was stirred at 50° C. for 5 hours. The reaction mixture was ice-cooled, 1N hydrochloric acid (2 ml) was added, and the mixture was sufficiently stirred at room temperature, and concentrated under reduced pressure. The obtained residue was dissolved in 0.1N hydrochloric acid, the mixture was washed twice with ethyl acetate, and the aqueous layer was freeze-dried. Ethanol (10 ml) and 10% palladium-carbon (45 mg) were added to the residue, and the mixture was stirred for 5 hours under hydrogen atmosphere. After filtration through celite, the solvent was evaporated under reduced pressure, and the obtained residue was purified by reversed-phase HPLC in the same manner as in Step 4 of Example 1 to give the title compound.

yield 46.6 mg (0.0746 mmol, 26%)
MS (ESI, m/z) 397 (MH+)
$^1$H-NMR (DMSO-d$_6$) δ 1.86 (2H, quint), 2.06 (2H, quint), 3.34 (2H, t), 3.56 (2H, t), 4.45 (2H, br), 4.69 (2H, br), 6.99 (1H, d), 7.41 (1H, dd), 7.52 (1H, d), 7.79 (2H, d), 8.13 (2H, d), 8.95 (1H, s), 9.02 (2H, s), 9.06 (2H, s), 9.39 (1H, s).

Example 7

2-{5-amidino-2-hydroxyphenoxy}ethyl 4-[(1-(1-iminoethyl)piperidin-4-yl)oxy]benzoate ditrifluoroacetate Step 1. Synthesis of 3-bromoethyl 4-(piperidin-4-yloxy)benzoate.

Using 4-{[1-(tert-butoxycarbonyl)piperidin-4-yloxybenzoate (5.00 g, 15.5 mmol) as a starting material and in the same manner as; in Step 2 of Example 2, the title compound was obtained. This compound in a crude state was used for the next reaction.

MS (ESI, m/z) 328 (MH+)

Step 2. Synthesis of 2-bromoethyl 4-[(1-(1-iminoethyl)piperidin-4-yl)oxy]benzoate trifluoroacetate.

3-Bromoethyl 4-(piperidin-4-yloxy)benzoate (about 14.8 mmol) obtained in Step 1 was dissolved in anhydrous ethanol (70 ml), and ethyl acetimidate hydrochloride (3.66 g, 29.6 mmol) and diisopropylethylamine (10.3 ml, 59.2 mmol) were added. The mixture was stirred at room temperature overnight, and concentrated under reduced pressure, and the residue was purified by reversed-phase HPLC in the same manner as in Step 4 of Example 1 to give the title compound.

yield 4.87 g (10.1 mmol, 65%)
MS (ESI, m/12) 369 (MH+)

Step 3. Synthesis of 2-[5-amidino-2-(benzyloxy)phenoxy]ethyl 4-[(1-(1-iminoethyl)piperidin-4-yl)oxy]benzoate ditrifluoroacetate.

To 2-bromoethyl 4-[(1-(1-iminoethyl)piperidin-4-yl)oxy]benzoate trifluoroacetate (254 mg, 0.526 mmol) obtained in Step 2,4-(benzyloxy)-3-hydroxybenzamidine trifluoroacetate (187 mg, 0.526 mmol) obtained in Step 2 of Example 6, and cesium carbonate (51.5 mg, 1.58 mmol) was added anhydrous N,N-dimethylformamide (5 ml), and the mixture was stirred at 50° C. overnight. 1N Hydrochloric acid (3.2 ml) was added under ice-cooling, the mixture was concentrated under reduced pressure, and the obtained residue was purified by reversed-phase HPLC in the same manner as in Step 4 of Example 1 to give the title compound.

yield 71.0 mg (0.0936 mmol, 18%)

MS (ESI, m/z) 531 (MH+)

Step 4. Synthesis of 2-{5-amidino-2-hydroxyphenoxy}ethyl 4-[(1-(1-iminoethyl)piperidin-4-yl)oxy]benzoate ditrifluoroacetate.

2-[5-Amidino-2-(benzyloxy)phenoxy]ethyl 4-[(1-(1-iminoethyl)piperidin-4-yl)oxy]benzoate ditrifluoroacetate (71 mg, 0.0936 mmol) obtained in Step 3 was dissolved in ethanol (2 ml), 10% palladium-carbon (7 mg) was added thereto, and the mixture was stirred for 2 hours under hydrogen atmosphere. After filtration through celite, the solvent was evaporated under reduced pressure, and the obtained residue was purified by reversed-phase HPLC in the same manner as in Step 4 of Example 1 to give the title compound.

yield 56.7 mg (0.0847 mmol, 91%)

MS (ESI, m/2) 440 (MH+)

$^1$H-NMR (DMSO-$d_6$) δ 1.79 (2H, br), 2.08 (2H, br), 2.30 (3H, s), 3.52-3.58 (2H, m), 3.72-3.73 (2H, m), 4.42 (2H, br), 4.61 (2H, br), 4.85 (1H, br), 7.00 (1H, dd), 7.12 (2H, d), 7.40-7.44 (1H, m), 7.53-7.54 (1H, m), 7.91 (2H, dd), 8.70 (1H, s), 9.09 (2H, s), 9.16 (2H, s), 9.25 (1H, s).

Example 8

2-{5-amidino-2-hydroxyphenoxy}ethyl 4-({1-amidinopiperidin-4-yl}oxy)benzoate ditrifluoroacetate Step 1. Synthesis of 2-bromoethyl 4-({1-amidinopiperidin-4-yl}oxy)benzoate trifluoroacetate.

3-Bromoethyl 4-(piperidin-4-yloxy)benzoate trifluoroacetate (540 mg, 1.22 mmol) and 1H-pyrazole-1-carboxamidine hydrochloride (215 mg) were dissolved in anhydrous acetonitrile (12 ml), diisopropylethylamine (425 μl) was added thereto, and the mixture was stirred for 3.5 hours. The reaction mixture was concentrated under reduced pressure, and the residue was purified by reversed-phase HPLC in the same manner as in Step 4 of Example 1 to give the title compound.

yield 224 mg (0.463 mmol, 38%)

MS (ESI, m/2) 370 (MH+)

Step 2. Synthesis of 2-[5-amidino-2-(benzyloxy)phenoxy]ethyl 4-({1-amidinopiperidin-4-yl}oxy)benzoate ditrifluoroacetate.

Using 2-bromoethyl 4-({1-amidinopiperidin-4-yl}oxy)benzoate trifluoroacetate (224 mg, 0.463 mmol) obtained in Step 1, 4-(benzyloxy)-3-hydroxybenzamidine trifluoroacetate (165 mg, 0.463 mmol) obtained in Step 2 of Example 6, and cesium carbonate 45.3 mg (1.39 mmol) and in the same manner as in Step 3 of Example 7, the title compound was obtained.

yield 137 mg (0.181 mmol, 39%)

MS (ESI, m/z) 531 (MH+)

Step 3. Synthesis of 2-{5-amidino-2-hydroxyphenoxy}ethyl 4-({1-amidinopiperidin-4-yl}oxy)benzoate ditrifluoroacetate.

Using 2-[5-amidino-2-(benzyloxy)phenoxy]ethyl 4-({1-amidinopiperidin-4-yl}oxy)benzoate ditrifluoroacetate (137 mg, 0.181 mmol) obtained in Step 2 and 10% palladium-carbon (14 mg) and in the same manner as in Step 4 of Example 7, the title compound was obtained.

MS (ESI, m/z) 441 (MH+)

$^1$H-NMR (DMSO-$d_6$) δ 1.63-1.71 (2H, m), 2.00-2.08 (2H, m), 3.34-3.41 (2H, m), 3.64-3.70 (2H, m), 4.41 (2H, br), 4.60 (2H, br), 4.75-4.80 (1H, m), 6.98 (1H, d), 7.11 (2H, d), 7.40 (1H, dd), 7.47 (4H, s), 7.50 (1H, d), 7.90 (22H, d), 8.94 (1H, s), 9.05 (1H, s).

Example 9

2-(5-amidino-2-hydroxyphenoxy)ethyl 1-(1-iminoethyl)-4-methylpiperidine-4-carboxylate ditrifluoroacetate Step 1. Synthesis of 2-bromoethyl 1-(1-iminoethyl)-4-methylpiperidine-4-carboxylate.

1-tert-Butyl 4-ethyl 4-methylpiperidine-1,4-dicarboxylate (250 mg, 0.92 mmol) obtained in Step 1 of Example 4 was dissolved in 4N hydrochloric acid/1,4-dioxane (8 ml), and the mixture was stirred at room temperature for 2 hours. The solvent was evaporated under reduced pressure, and the obtained residue was dissolved in ethanol (9 ml). Ethyl acetimidate hydrochloride (228 mg, 1.84 mmol) and diisopropylethylamine (642 ml, 3.69, mmol) were added thereto, and the mixture was stirred at room temperature for 2 days. The solvent was evaporated under reduced pressure, and the obtained residue was dissolved in 2-bromoethanol (2.5 ml). p-Toluenesulfonic acid monohydrate (5 mg) was added, and the mixture was stirred at 90° C. for two nights. The solvent was evaporated under reduced pressure, and the obtained residue was purified by reversed-phase HPLC in the same manner as in Step 4 of Example 1 to give the title compound.

yield 298 mg (0.735 mmol, 80%)

MS (ESI, m/z) 292 (MH+)

Step 2. Synthesis of 2-(5-amidino-2-hydroxyphenoxy)ethyl 1-(1-iminoethyl)-4-methylpiperidine-4-carboxylate ditrifluoroacetate.

Using 2-bromoethyl 1-(1-iminoethyl)-4-methylpiperidine-4-carboxylate (96 mg, 0.24 mmol) obtained in Step 1 and in the same manner as in Step 3 of Example 6, the title compound was obtained.

yield 24.8 mg (0.042 mmol, 18%)

MS (ESI, m/z) 363 (MH+)

$^1$H-NMR (DMSO-$d_6$) δ 1.19 (3H, s), 1.56 (2H, ddd), 2.05 (2H, ddd), 2.24 (3H, s), 3.26 (2H, ddd), 3.77 (2H, ddd), 4.31 (2H, br), 4.48 (2H, br), 6.99 (1H, d), 7.40 (1H, d), 7.47 (1H, s), 8.58 (1H, s), 9.07 (4H, s), 9.18 (1H, s).

Example 10

2-(5-amidino-2-hydroxyphenoxy)ethyl 1-amidino-4-methylpiperidine-4-carboxylate ditrifluoroacetate Using 1H-pyrazole-1-carboxamidine hydrochloride instead of ethyl acetimidate hydrochloride and in the same manner as in Step 1 and 2 of Example 9, the title compound was obtained.

MS (ESI, m/z) 364 (MH+)

$^1$H-NMR (DMSO-$d_6$) δ 1.18 (3H, s), 1.45 (2H, ddd), 2.00 (2H, ddd), 3.14 (2H, ddd), 3.62 (2H, ddd), 4.30 (2H, br), 4.47 (2H, br), 6.98 (1H, d), 7.40 (1H, dd), 7.46 (1H, d), 7.50 (4H, s), 9.07 (2H, s), 9.13 (2H, s).

Example 11

(2R)-3-{5-amidino-2-hydroxyphenoxy}-2-propyl 4-[imino(pyrrolidin-1-yl)methyl]benzoate ditrifluoroacetate Step 1. Synthesis of (2R)-3-{[(4-methylphenyl)sulfonyl]oxy}-2-propyl 4-[imino(pyrrolidin-1-yl)methyl]benzoate trifluoroacetate.

4-[Imino(pyrrolidin-1-yl)methyl]benzoic acid hydrochloride (100 mg, 0.39 mmol) obtained in Step 2 of Example 2, (2R)-1,2-propanediol-1-tosylate (1 g) and p-toluenesulfonic acid monohydrate (10 mg) were heated at 90° C. for 3 days. The residue was purified by reversed-phase HPLC in the same manner as in Step 4 of Example 1 to give the title compound.

yield 45.1 mg (0.083 mmol, 21%)

MS (ESI, m/z) 431 (MH+)

Step 2. Synthesis of (2R)-3-bromo-2-propyl 4-[imino(pyrrolidin-1-yl)methyl]benzoate trifluoroacetate.

(2R)-3-{[(4-methylphenyl)sulfonyl]oxy}-2-propyl 4-[imino(pyrrolidin-1-yl)methyl]benzoate trifluoroacetate (45.1 mg, 0.083 mmol) obtained in Step 1 was dissolved in DMF (2 ml), lithium bromide (72 mg, 0.83 mmol) was added thereto, and the mixture was stirred at 50° C. for 2 days. The solvent was evaporated under reduced pressure, and the obtained residue was purified by reversed-phase HPLC in the same manner as in Step 4 of Example 1 to give the title compound.

yield 29.1 mg (0.064 mmol, 77%)

MS (ESI, m/z) 340 (MH+)

$^1$H-NMR (DMSO-d$_6$) δ 1.41 (3H, d), 1.86 (2H, quint), 2.06 (2H, quint), 3.36 (2H, t), 3.56 (2H, t), 3.77 (1H, dd), 3.85 (1H, dd), 5.29 (1H, ddd), 7.81 (2H, d), 8.15 (2H, d), 8.96 (1H, s), 9.38 (1H, s).

Step 3. Synthesis of (2R)-3-{5-amidino-2-hydroxyphenoxy}-2-propyl 4-[imino(pyrrolidin-1-yl)methyl]benzoate ditrifluoroacetate.

Using (1R)-2-bromo-1-methylethyl 4-[imino(pyrrolidin-1-yl)methyl]benzoate trifluoroacetate (29.1 mg, 0.064 mmol) obtained in Step 2 and in the same manner as in Step 3 of Example 6, the title compound was obtained.

yield 2.4 mg (0.004 mmol, 6%)

MS (ESI, m/z) 411 (MH+)

Example 12

{4-amidino-2-[2-({4-[imino(pyrrolidin-1-yl)methyl]benzoyl}oxy)ethoxy]phenoxy}acetic acid ditrifluoroacetate Step 1. Synthesis of 2-{5-amidino-2-[benzyloxycarbonylmethoxy]phenoxy}ethyl 4-[imino(pyrrolidin-1-yl)methyl]benzoate ditrifluoroacetate.

The compound of Example 6 (50 mg, 0.08 mmol) was dissolved in DMF (0.8 ml), benzyl bromoacetate (12.7 μL, 0.08 mmol) and potassium carbonate (33 mg, 0.24 mmol) were added thereto, and the mixture was stirred at 40° C. overnight. The reaction was quenched with 1N hydrochloric acid (1 ml), the solvent was evaporated under reduced pressure, and the obtained residue was purified by reversed-phase HPLC in the same manner as in Step 4 of Example 1 to give the title compound.

yield 12.8 mg (0.017 mmol, 21%)

MS (ESI, m/z) 545 (MH+)

Step 2. Synthesis of {4-amidino-2-[2-({4-[imino(pyrrolidin-1-yl)methyl]benzoyl}oxy)ethoxy]phenoxy}acetic acid ditrifluoroacetate.

2-{5-Amidino-2-[benzyloxycarbonylmethoxy]phenoxy}ethyl 4-[imino(pyrrolidin-1-yl)methyl]benzoate ditrifluoroacetate (12.8 mg, 0.017 mmol) obtained in Step 1 was dissolved in ethanol (1 ml), 10% palladium-carbon (5 mg) was added thereto, and the mixture was stirred for 3 hours under hydrogen atmosphere. After filtration through celite, the solvent was evaporated under reduced pressure, and the obtained residue was purified by reversed-phase HPLC in the same manner as in Step 4 of Example 1 to give the title compound.

yield 10.1 mg (0.015 mmol, 87%)

MS (ESI, m/z) 455 (MH+)

$^1$H-NMR (DMSO-d$_6$) δ 1.84 (2H, quint), 2.04 (2H, quint), 3.34 (2H, t), 3.56 (2H, t), 4.48 (2H, br), 4.69 (2H, br), 4.84 (2H, s), 7.11 (1H, d), 7.47 (1H, dd), 7.55 (1H, d), 7.79 (2H, d), 8.13 (2H, d), 8.94 (1H, s), 9.14 (2H, s), 9.17 (2H, s), 9.39 (1H, s).

Example 13

2-[5-amidino-2-(2-hydroxyethoxy)phenoxy]ethyl 4-[imino(pyrrolidin-1-yl)methyl]benzoate ditrifluoroacetate Step 1. Synthesis of 2-{5-amidino-2-[2-(benzyloxy)ethoxy]phenoxy}ethyl 4-[imino(pyrrolidin-1-yl)methyl]benzoate ditrifluoroacetate.

An operation in the same manner as in Step 1 of Example 12 was performed using benzyl 2-bromoethyl ether (12.5 μL, 0.08 mmol) instead of benzyl bromoacetate, and potassium carbonate (33 mg, 0.24 mmol), and the mixture was stirred at 40° C. overnight. The reaction was quenched with 1N hydrochloric acid (1 ml), the solvent was evaporated under reduced pressure, and the obtained residue was purified by reversed-phase HPLC in the same manner as in Step 4 of Example 1 to give the title compound.

yield 22.3 mg (0.029 mmol, 37%)

MS (ESI, m/z) 531 (MH+)

Step 2. Synthesis of 2-[5-amidino-2-(2-hydroxyethoxy)phenoxy]ethyl 4-[imino(pyrrolidin-1-yl)methyl]benzoate ditrifluoroacetate.

2-{5-Amidino-2-[2-(benzyloxy)ethoxy]phenoxy}ethyl 4-[imino(pyrrolidin-1-yl)methyl]benzoate ditrifluoroacetate (22.3 mg, 0.029 mmol) obtained in Step 1 was dissolved in acetic acid (1 ml), 10% palladium-carbon (5 mg) was added thereto, and the mixture was stirred for 3 hours under hydrogen atmosphere. After filtration through celite, the solvent was evaporated under reduced pressure, and the obtained residue was purified by reversed-phase HPLC in the same manner as in Step 4 of Example 1 to give the title compound.

yield 14.0 mg (0.021 mmol, 72%)

MS (ESI, m/z) 441 (MH+)

$^1$H-NMR (DMSO-d$_6$) δ 1.87 (2H, quint), 2.06 (2H, quint), 3.34 (2H, t), 3.56 (2H, t), 3.70 (2H, t), 4.11 (2H, t), 4.47 (2H, br), 4.70 (2H, br), 7.23 (1H, d), 7.53 (1H, dd), 7.56 (1H, d), 7.79 (2H, d), 8.12 (2H, d), 8.98 (1H, s), 9.17 (2H, s), 9.24 (2H, s), 9.41 (1H, s).

Example 14

[4-amidino-2-(2-{[4-({1-(1-iminoethyl)piperidin-4-yl}oxy)benzoyl]oxy}ethoxy)phenoxy]acetic acid ditrifluoroacetate The compound of Example 7 (200 mg, 0.299 mmol) and potassium carbonate (124 mg, 0.897 mmol) were suspended in acetonitrile (3 ml), benzyl bromoacetate (56.9 μl, 0.359 mmol) was added thereto, and the mixture was stirred at 40° C. overnight. 1N Hydrochloric acid (1.8 ml) was added under ice-cooling, and the mixture was concentrated under reduced pressure. The obtained residue was dissolved in ethanol (3 ml), 10% palladium-carbon (45 mg) was added thereto, and the mixture was stirred overnight under hydrogen atmosphere. After filtration through celite, the solvent was evaporated under reduced pressure, and the obtained residue was purified by reversed-phase HPLC in the same manner as in Step 4 of Example 1 to give the title compound.

yield 53.8 mg (0.074 mmol, 25%)

MS (ESI, m/z) 498 (MH+)

$^1$H-NMR (DMSO-d$_6$) δ 1.75-1.83 (2H, m), 2.00-2.06 (2H, m), 2.29 (3H, s), 3.40-3.56 (4H, m), 4.46 (2H, br), 4.61 (2H, br), 4.80 (1H, br), 4.85 (2H, s), 7.10 (2H, d), 7.11 (1H, d), 7.47 (1H, d), 7.52 (1H, dd), 7.92 (2H, d), 8.59 (1H, s), 8.87 (1H, s), 9.14 (4H, s).

Example 15

[4-amidino-2-(2-{[4-({1-amidinopiperidin-4-yl}oxy) benzoyl]oxy}ethoxy)phenoxy]acetic acid ditrifluoroacetate Step 1. Synthesis of 2-{5-amidino-2-[benzyloxycarbonylmethoxy}ethyl 4-({1-amidinopiperidin-4-yl}oxy)benzoate ditrifluoroacetate.

The compound of Example 8 (740 mg, 1.11 mmol) and potassium carbonate (459 mg, 3.31 mmol) were suspended in dehydrated DMF, benzyl bromoacetate (211 μl, 1.33 mmol) was added thereto, and the mixture was stirred at 40° C. for 3 hours. 1N Hydrochloric acid (7 ml) was added under ice-cooling, the mixture was concentrated under reduced pressure, and the obtained residue was purified by reversed-phase HPLC in the same manner as in Step 4 of Example 1 to give the title compound.

yield 445 mg (0.544 mmol, 49%)

MS (ESI, m/z) 589 (MH+)

Step 2. Synthesis of [4-amidino-2-(2-{[4-({1-amidinopiperidin-4-yl}oxy)benzoyl]oxy}ethoxy)phenoxy]acetic acid ditrifluoroacetate.

2-{5-Amidino-2-[benzyloxycarbonylmethoxy}ethyl 4-({1-amidinopiperidin-4-yl}oxy)benzoate ditrifluoroacetate (445 mg, 0.544 mmol) obtained in Step 1 and 10% palladium-carbon (70 mg) were suspended in a mixed solvent of ethanol (15 ml), 1,4-dioxane (2 ml) and water (4 ml), and the mixture was stirred for 2 hours under hydrogen atmosphere. After filtration through celite, the solvent was evaporated under reduced pressure, and the obtained residue was purified by reversed-phase HPLC in the same manner as in Step 4 of Example 1 to give the title compound.

yield 375 mg (0.515 mmol, 95%)

MS (ESI, m/z) 499 (MH+)

$^1$H-NMR (DMSO-d$_6$) δ 1.63-1.70 (2H, m), 2.00-2.06 (2H, m), 3.35-3.41 (2H, m), 3.65-3.69 (2H, m), 4.44 (2H, br), 4.61 (2H, br), 4.76-4.80 (1H, m), 4.85 (2H, s), 7.09-7.12 (3H, m), 7.45 (1H, d), 7.50 (4H, s), 7.54 (1H, d), 7.91 (2H, d), 9.14 (4H, d).

Example 16

2-{3-amidinophenoxy}ethyl 4-[(1-(1-iminoethyl) piperidin-4-yl)oxy]benzoate ditrifluoroacetate Step 1. Synthesis of benzyl 4-{4-[(2-bromoethoxy)carbonyl] phenoxy}piperidine-1-carboxylate.

3-Bromoethyl 4-(piperidin-4-yloxy)benzoate trifluoroacetate (11.0 g, 24.9 mmol) was dissolved in dichloromethane (150 ml), and triethylamine (5.20 ml, 37.3 mmol) and benzyloxycarbonyl chloride (5.27 ml, 37.3 mmol) were added thereto under ice-cooling. The mixture was stirred at room temperature for 4 hours, and ice-cooled. N,N-Dimethylethylenediamine (4.1 ml, 37.3 mmol) was added thereto, the mixture was stirred at room temperature for 30 minutes. Saturated aqueous sodium hydrogencarbonate solution (100 ml) was added thereto, and the mixture was concentrated under reduced pressure. The obtained residue was diluted with ethyl acetate, and the organic layer was washed with 1N hydrochloric acid and saturated brine, and dried over anhydrous sodium sulfate. The solvent was evaporated under reduced pressure, and the residue was purified by silica gel chromatography (hexane:ethyl acetate 9:1-4:1) to give the title compound.

yield 4.99 g (10.8 mmol, 43%)

MS (ESI, m/z) 462 (MH+)

Step 2. Synthesis of 2-{3-amidinophenoxy}ethyl 4-(piperidin-4-yloxy)benzoate.

3-Hydroxybenzamidine trifluoroacetate (298 mg, 1.19 mmol) obtained in Step 1 of Example 2, benzyl 4-{4-[(2-bromoethoxy)carbonyl]phenoxy}piperidine-1-carboxylate (500 mg, 1.08 mmol), and cesium carbonate (717 mg, 2.20 mmol) were suspended in dehydrated DMF, and the mixture was stirred at 50° C. for 6 hours. The reaction mixture was ice-cooled, and 1N hydrochloric acid (4.5 ml) was added to the mixture and the mixture was concentrated under reduced pressure. The obtained residue was diluted with ethyl acetate, and the mixture was washed with 0.1N hydrochloric acid and saturated brine, and dried over anhydrous sodium sulfate. The solvent was evaporated, and the obtained crude product (about 700 mg) was dissolved in ethanol (15 ml). 10% Palladium-carbon (105 mg) was added thereto, and the mixture was stirred for 5.5 hours under hydrogen atmosphere. After filtration through celite, the solvent was evaporated to give the title compound as a crude product. This compound in a crude state was used for the next reaction.

yield 538 mg (1.4 mmol, quantitative)

Step 3. Synthesis of 2-{3-amidinophenoxy}ethyl 4-[(1-(1-iminoethyl)piperidin-4-yl)oxy]benzoate ditrifluoroacetate.

Using 2-{3-amidinophenoxy}ethyl 4-(piperidin-4-yloxy) benzoate 179 mg (0.467 mmol) obtained in Step 2 as a starting material and according to the synthetic method of Step 2 of Example 7, the title compound was obtained.

yield 70.4 mg (0.108 mmol, 23%)

MS (ESI, m/z) 424 (MH+)

$^1$H-NMR (DMSO-d$_6$) δ 1.78 (2H, br), 2.08 (2H, br), 2.31 (3H, s), 3.52-3.59 (2H, m), 3.73-3.83 (2H, m), 4.45 (2H, br), 4.62 (2H, br), 4.82-4.88 (1H, m), 7.13 (2H, d), 7.35-7.38 (1H, m), 7.42-7.47 (2H, m), 7.55 (1H, t), 7.92 (2H, d), 8.72 (1H, s), 9.27 (1H, s), 9.34 (2H, s), 9.56 (2H, s).

Example 17

2-{3-amidinophenoxy}ethyl 4-({1-amidinopiperidin-4-yl}oxy)benzoate ditrifluoroacetate Using 2-{3-amidinophenoxy}ethyl 4-(piperidin-4-yloxy) benzoate (179 mg, 0.467 mmol) as a starting material and according to the synthetic method of Step 1 of Example 8, the title compound was obtained.

yield 66.2 mg (0.101 mmol, 22%)

MS (ESI, m/z) 425 (MH+)

$^1$H-NMR (DMSO-d$_6$) δ 1.64-1.72 (2H, m), 2.00-2.08 (2H, m), 3.37-3.43 (2H, m), 3.65-3.71 (2H, m), 4.44 (2H, br), 4.62 (2H, br), 4.78-4.93 (1H, m), 7.12 (2H, d), 7.35-7.38 (1H, m), 7.42-7.47 (2H, m), 7.55 (1H, t), 7.62 (4H, s), 7.92 (2H, d), 9.34 (2H, s), 9.57 (2H, s).

Example 18

2-{5-amidino-2-methoxyphenoxy}ethyl 4-[imino(pyrrolidin-1-yl)methyl]benzoate ditrifluoroacetate

Using iodomethane instead of benzyl bromoacetate and in the same manner as in Step 1 of Example 12, the title compound was obtained.

yield 6.8 mg (0.011 mmol, 27%)
MS (ESI, m/z) 411 (MH+)
$^1$H-NMR (DMSO-$d_6$) δ 1.86 (2H, quint), 2.06 (2H, quint), 3.34 (2H, t), 3.56 (2H, t), 3.84 (3H, s), 4.46 (2H, br), 4.70 (2H, br), 7.20 (1H, d), 7.53 (1H, dd), 7.54 (1H, d), 7.80 (2H, d), 8.13 (2H, d), 8.96 (1H, s), 9.13 (2H, s), 9.17° (2H, s), 9.40 (1H, s).

Example 19

2-{5-amidino-2-ethoxyphenoxy}ethyl 4-[imino(pyrrolidin-1-yl)methyl]benzoate ditrifluoroacetate

Using iodoethane instead of benzyl bromoacetate and in the same manner as in Step 1 of Example 12, the title compound was obtained.

yield 10 mg (0.016 mmol, 38%)
MS (ESI, m/z) 425 (MH+)
$^1$H-NMR (DMSO-$d_6$) δ 1.29 (3H, t), 1.87 (2H, quint), 2.06 (2H, quint), 3.34 (2H, t), 3.56 (2H, t), 4.12 (2H, q), 4.46 (2H, br), 4.70 (2H, br), 7.18 (1H, d), 7.53 (1H, dd), 7.57 (1H, d), 7.80 (2H, d), 8.12 (2H, d), 8.98 (1H, s), 9.17 (4H, s), 9.42 (1H, s).

Example 20

2-[5-amidino-2-(cyanomethoxy)phenoxy]ethyl 4-[imino(pyrrolidin-1-yl)methyl]benzoate ditrifluoroacetate

Using iodoacetonitrile instead of benzyl bromoacetate and in the same manner as in Step 1 of Example 12, the title compound was obtained.

yield 277 mg (0.417 mmol, 52%)
MS (ESI, m/z) 435 (MH+)
$^1$H-NMR (DMSO-$d_6$) δ 1.84 (2H, quint), 2.04 (2H, quint), 3.32 (2H, t), 3.54 (2H, t), 4.48 (2H, br), 4.70 (2H, br), 5.27 (2H, s), 7.34 (1H, d), 7.53 (1H, dd), 7.59 (1H, d), 7.77 (2H, d), 8.13 (2H, d), 8.93 (1H, s), 9.23 (4H, s), 9.38 (1H, s).

Example 21

2-(5-amidino-2-{[(dimethylamino)thiocarbonyl]oxy}phenoxy)ethyl 4-{imino(pyrrolidin-1-yl)methyl}benzoate ditrifluoroacetate

Using N,N-dimethylthiocarbamoyl chloride instead of benzyl bromoacetate and in the same manner as in Step 1 of Example 12, the title compound was obtained.

yield 4 mg (0.006 mmol, 14%)
MS (ESI, m/z) 484 (MH+)
$^1$H-NMR (DMSO-$d_6$) δ 1.90 (2H, quint), 2.01 (2H, quint), 3.16 (3H, s), 3.24 (3H, s), 3.35 (2H, t), 3.86 (2H, t), 4.46 (2H, br), 4.69 (2H, br), 7.00 (1H, d), 7.41 (1H, dd), 7.52 (1H, d), 7.63 (2H, d), 8.13 (2H, d), 8.97 (2H, s), 9.07 (2H, s), 9.28 (1H, s), 9.34 (1H, s).

Example 22

2-[5-amidino-2-(cyclopropylmethoxy)phenoxy]ethyl 4-[imino(pyrrolidin-1-yl)methyl]benzoate ditrifluoroacetate

Using (bromomethyl)cyclopropane instead of benzyl bromoacetate and in the same manner as in Step 1 of Example 12, the title compound was obtained.

yield 5.35 mg (0.00788 mmol, 16%)
MS (ESI, m/z) 450 (MH+)
$^1$H-NMR (DMSO-$d_6$) δ 0.26-0.28 (2H, m), 0.47-0.52 (2H, m), 1.17 (1H, br), 1.81-1.87 (2H, m), 2.01-2.06 (2H, m), 3.31 (2H, br), 3.54 (2H, br), 3.91 (2H, d), 4.45 (2H, br), 4.69 (2H, br), 7.16 (1H, d), 7.47-7.53 (2H, m), 7.78 (2H, d), 8.11 (2H, d), 8.93 (1H, s), 9.05 (2H, s), 9.13 (2H, s), 9.38 (1H, s).

Example 23

2-{5-amidino-2-propoxyphenoxy}ethyl 4-[imino(pyrrolidin-1-yl)methyl]benzoate ditrifluoroacetate

Using n-propyl bromide instead of benzyl bromoacetate and in the same manner as in Step 1 of Example 12, the title compound was obtained.

yield 4.94 mg (0.00741 mmol, 15%)
MS (ESI, m/z) 438 (MH+)
$^1$H-NMR (DMSO-$d_6$) δ 0.89 (3H, t), 1.66 (2H, sext), 1.83-1.89 (2H, m), 2.00-2.07 (2H, m), 3.31 (2H, t), 3.54 (2H, t), 4.00 (2H, t), 4.43 (2H, br), 4.68 (2H, br), 7.18 (1H, d), 7.49-7.52 (2H, m), 7.77 (2H, d), 8.10 (2H, d), 8.92 (1H, s), 9.05 (2H, s), 9.13 (2H, s), 9.38 (1H, s).

Example 24

2-{5-amidino-2-isobutoxyphenoxy}ethyl 4-[imino(pyrrolidin-1-yl)methyl]benzoate ditrifluoroacetate

Using isobutyl bromide instead of benzyl bromoacetate and in the same manner as in Step 1 of Example 12, the title compound was obtained.

yield 6.94 mg (0.0102 mmol, 21%)
MS (ESI, m/z) 452 (MH+)
$^1$H-NMR (DMSO-$d_6$) δ 0.89 (6H, d), 1.82-2.06 (5H, m), 3.30 (2H, t), 3.54 (2H, t), 3.80 (2H, d), 4.42 (2H, br), 4.68 (2H, br), 7.17 (1H, d), 7.48-7.52 (2H, m), 7.76 (2H, d), 8.09 (2H, d), 8.94 (1H, s), 9.13 (4H, d), 9.38 (1H, s).

Example 25

2-{5-amidino-2-(2-pyrrolidin-1-ylethoxy)phenoxy}ethyl 4-[imino(pyrrolidin-1-yl)methyl]benzoate tritrifluoroacetate

Using 1-(2-chloroethyl)pyrrolidine hydrochloride instead of benzyl bromoacetate, sodium iodide and in the same manner as in Step 1 of Example 12, the title compound was obtained.

yield 10.3 mg (0.0123 mmol, 26%)
MS (ESI, m/z) 493 (MH+)
$^1$H-NMR (DMSO-$d_6$) δ 1.72-1.87 (4H, m), 2.03 (2H, q), 3.10 (2H, br), 3.31 (2H, t), 3.52-3.60 (6H, m), 4.38-4.46 (4H, m), 4.68 (2H, br), 7.26 (1H, d), 7.49-7.57 (2H, m), 7.78 (2H, d), 8.11 (2H, d), 8.96 (1H, s), 9.21-9.23 (4H, m), 9.41 (1H, s).

Example 26

2-{2-(2-aminoethoxy)-5-amidinophenoxy}ethyl 4-[imino(pyrrolidin-1-yl)methyl]benzoate tritrifluoroacetate Step 1. Synthesis of 2-(5-amidino-2-{2-[(tert-butoxycarbonyl)amino]ethoxy}phenoxy)ethyl 4-[imino(pyrrolidin-1-yl)methyl]benzoate ditrifluoroacetate.

Using 2-(tert-butoxycarbonyl)aminoethyl bromide instead of benzyl bromoacetate and in the same manner as in Step 1 of Example 12, the title compound was obtained.
yield 30.7 mg (0.0400 mmol, 28%)
MS (ESI, m/z) 539 (MH+)

Step 2. Synthesis of 2-{2-(2-aminoethoxy)-5-amidinophenoxy}ethyl 4-[imino(pyrrolidin-1-yl)methyl]benzoate tritrifluoroacetate.

To 2-(5-amidino-2-{2-[(tert-butoxycarbonyl)amino]ethoxy}phenoxy)ethyl 4-[imino(pyrrolidin-1-yl)methyl]benzoate ditrifluoroacetate (30.7 mg, 0.0400 mmol) obtained in Step 1 were added anhydrous 1,4-dioxane (0.5 ml), dehydrated DMF (1 ml) and 4N hydrochloric acid/1,4-dioxane (2 ml), and the mixture was stirred at room temperature for 50 minutes. The solvent was evaporated under reduced pressure, and the obtained residue was purified by reversed-phase HPLC in the same manner as in Step 4 of Example 1 to give the title compound.
yield 32.0 mg (0.0409 mmol, 100%)
MS (ESI, m/z) 439 (MH+)
$^1$H-NMR (DMSO-$d_6$) δ 1.80-1.89 (2H, m), 2.00-2.06 (2H, m), 3.18-3.34 (4H, m), 3.55 (2H, t), 4.28 (2H, t), 4.48 (2H, br), 4.69 (2H, br), 7.26 (1H, d), 7.53 (1H, dd), 7.60 (1H, d), 7.77 (2H, d), 8.10 (2H, d), 8.18 (3H, br), 8.99 (1H, s), 9.23 (2H, s), 9.36 (2H, s), 9.42 (1H, s).

Example 27

2-{2-[2-(acetamido)ethoxy]-5-amidinophenoxy}ethyl 4-[imino(pyrrolidin-1-yl)methyl]benzoate ditrifluoroacetate The compound of Example 26 (30.2 mg, 0.0386 mmol) was dissolved in pyridine (390 μl), acetic anhydride (3.65 μl, 0.0386 mmol) was added thereto, and the mixture was stirred at room temperature for 1 hour. The solvent was evaporated under reduced pressure, and the obtained residue was purified by reversed-phase HPLC in the same manner as in Step 4 of Example 1 to give the title compound.
yield 30.0 mg (0.0422 mmol, 109%)
MS (ESI, m/z) 481 (MH+)
$^1$H-NMR (DMSO-$d_6$) δ 1.73-1.89 (5H, m), 2.02-2.08 (2H, m), 3.32-3.37 (4H, m), 3.56 (2H, t), 4.07 (2H, t), 4.47 (2H, br), 4.68 (2H, br), 7.24 (1H, d), 7.51-7.57 (2H, m), 7.79 (2H, d), 8.11-8.13 (3H, m), 8.97 (1H, s), 9.18 (2H, s), 9.23 (2H, s), 9.41 (1H, s).

Example 28

2-{2-(acetoxy)-5-amidinophenoxy}ethyl 4-[imino(pyrrolidin-1-yl)methyl]benzoate ditrifluoroacetate Using acetyl chloride instead of benzyl bromoacetate and in the same manner as in Step 1 of Example 12, the title compound was obtained.
yield 7.52 mg (0.0113 mmol, 24%)
MS (ESI, m/z) 438 (MH+)
$^1$H-NMR (DMSO-$d_6$) δ 1.83-1.91 (2H, m), 2.02-2.11 (2H, m), 2.18-2.20 (3H, m), 3.35 (2H, t), 3.57 (2H, t), 4.47 (2H, br), 4.71 (2H, br), 7.36 (1H, d), 7.43-7.49 (1H, m), 7.64 (1H, d), 7.79-7.82 (2H, m), 8.13-8.16 (2H, m), 8.95 (1H, s), 9.34-9.41 (5H, m).

Example 29

2-(5-amidino-2-{[(dimethylamino)carbonyl]oxy}phenoxy)ethyl 4-[imino(pyrrolidin-1-yl)methyl]benzoate ditrifluoroacetate Using N,N-dimethylcarbamoyl chloride instead of benzyl bromoacetate and in the same manner as in Step 1 of Example 12, the title compound was obtained.
yield 4.31 mg (0.00605 mmol, 13%)
MS (ESI, m/z) 467 (MH+)
$^1$H-NMR (DMSO-$d_6$) δ 1.86 (2H, quint), 2.06 (12H, quint), 2.75 (3H, s), 2.92-3.01 (5H, m), 3.32 (2H, t), 3.55 (2H, t), 4.48 (2H, br), 4.68 (2H, br), 7.37 (1H, d), 7.45 (1H, dd), 7.61 (1H, d), 7.79 (12H, d), 8.14 (2H, d), 8.93 (1H, s), 9.23 (2H, s), 9.32 (2H, s), 9.39 (1H, s).

Example 30

4-amidino-2-[2-({4-[imino(pyrrolidin-1-yl)methyl]benzoyl}oxy)ethoxy]phenyl pyrrolidine-1-carboxylate ditrifluoroacetate Using 1-pyrrolidinecarbonyl chloride instead of benzyl bromoacetate, potassium hydrogencarbonate instead of potassium carbonate, and in the same manner as in Step 1 of Example 12, the title compound was obtained.
yield 9.43 mg (0.0131 mmol, 27%)
MS (ESI, m/z) 493 (MH+)
$^1$H-NMR (DMSO-$d_6$) δ 1.70-1.78 (4H, m), 1.85 (2H, quint), 2.04 (2H, quint), 3.14 (2H, t), 3.30 (2H, t), 3.38 (2H, t), 3.54 (2H, t), 4.46 (2H, br), 4.66 (2H, br), 7.34 (1H, d), 7.44 (1H, dd), 7.59 (1H, d), 7.78 (2H, d), 8.11 (2H, d), 8.93 (1H, s), 9.31 (4H, s), 9.39 (1H, s).

Example 31

3-{5-amidino-2-hydroxyphenoxy}propyl 4-[imino(pyrrolidin-1-yl)methyl]benzoate ditrifluoroacetate Step 1. Synthesis of 3-bromopropyl 4-[imino(pyrrolidin-1-yl)methyl]benzoate trifluoroacetate.

Ethyl 4-imino(pyrrolidin-1-yl)methyl]benzoate trifluoroacetate (706 mg, 1.96 mmol) and p-toluenesulfonic acid monohydrate (186 mg, 0.98 mmol) were dissolved in 3-bromo-1-propanol (5 ml), and the mixture was stirred at 90° C. overnight. The solvent was evaporated under reduced pressure, and the obtained residue was purified by reversed-phase HPLC in the same manner as in Step 4 of Example 1 to give the title compound.
yield 537 mg (1.19 mmol, 61%)
MS (ESI, m/z) 339 (MH+)

Step 2. Synthesis of 3-{5-amidino-2-hydroxyphenoxy}propyl 4-[imino(pyrrolidin-1-yl)methyl]benzoate ditrifluoroacetate.

Using 3-bromopropyl 4-[imino(pyrrolidin-1-yl)methyl]benzoate trifluoroacetate instead of 2-bromoethyl 4-[imino(pyrrolidin-1-yl)methyl]benzoate trifluoroacetate and in the same manner as in Step 3 of Example 6, the title compound was obtained.
yield 25.9 mg (0.0405 mmol, 26%)
MS (ESI, m/z) 410 (MH+)

¹H-NMR (DMSO-d₆) δ 1.84-1.91 (2H, m), 2.02-2.11 (2H, m), 2.23-2.29 (2H, m), 3.34 (2H, t), 3.56 (2H, t), 4.23 (2H, t), 4.53 (2H, t), 6.98 (1H, d), 7.38 (1H, dd), 7.45 (1H, d), 7.78 (2H, d), 8.17 (2H, d), 8.91-8.92 (3H, m), 9.05 (2H, s), 9.38 (1H, s).

Example 32

{4-amidino-2-[3-({4-[imino(pyrrolidin-1-yl)methyl]benzoyl}oxy)propoxy]phenoxy}acetic acid ditrifluoroacetate Step 1. Synthesis of 3-{5-amidino-2-[benzyloxycarbonylmethoxy]phenoxy}propyl 4-[imino(pyrrolidin-1-yl)methyl]benzoate trifluoroacetate.
Using the compound of Example 31 instead of the compound of Example 8 and in the same manner as in Step 1 of Example 15, the title compound was obtained.
yield 18.0 mg (0.0229 mmol, 46%)
MS (ESI, m/z) 558 (MH+)
Step 2. Synthesis of {4-amidino-2-[3-({4-[imino(pyrrolidin-1-yl)methyl]benzoyl}oxy)propoxy]phenoxy}acetic acid ditrifluoroacetate.
Using 3-{5-amidino-2-[benzyloxycarbonylmethoxy]phenoxy}propyl 4-[imino(pyrrolidin-1-yl)methyl]benzoate trifluoroacetate instead of 2-{5-amidino-2-[2-(benzyloxy)]-2-oxoethoxy}ethyl 4-({1-amidinopiperidin-4-yl)oxy}benzoate ditrifluoroacetate and in the same manner as in Step 2 of Example 15, the title compound was obtained.
yield 12.8 mg (0.0184 mmol, 80%)
MS (ESI, m/z) 468 (MH+)
¹H-NMR (DMSO-d₆) δ 1.84 (2H, quint), 2.04 (2H, quint), 2.24 (2H, quint), 3.32 (2H, t), 3.54 (2H, t), 4.25 (2H, t), 4.48 (2H, t), 4.81 (2H, s), 7.07 (1H, d), 7.43 (1H, dd), 7.47 (1H, d), 7.76 (2H, d), 8.15 (2H, d), 8.92 (1H, s), 9.13 (4H, d), 9.37 (1H, s).

Example 33

2-[5-amidino-2-(cyanomethoxy)phenoxy]ethyl 4-[(1-(1-iminoethyl)piperidin-4-yl)oxy]benzoate ditrifluoroacetate The compound of Example 7 (22 mg, 0.033 mmol) and potassium carbonate (14 mg, 0.101 mmol) were suspended in dehydrated DMF (2 ml), and iodoacetonitrile (6 μl, 0.036 mmol) was added thereto. The mixture was stirred at room temperature for 4 hours, and ice-cooled, and 1N hydrochloric acid 0.5 ml was added thereto. The mixture was concentrated under reduced pressure, and the obtained residue was purified by reversed-phase HPLC in the same manner as in Step 4 of Example 1 to give the title compound.
yield 15.3 mg (0.022 mmol, 66%)
MS (ESI, m/z) 480 (MH+)
¹H-NMR (DMSO-d₆) δ 1.75-1.83 (2H, m), 2.05-2.18 (2H, m), 2.30 (3H, s), 3.48-3.60 (2H, m), 3.70-3.8.5 (2H, m), 4.47 (2H, br), 4.64 (2H, br), 4.84 (1H, br), 5.30 (2H, s), 7.12 (2H, d), 7.36 (1H, d), 7.54 (1H, dd), 7.61 (1H, d), 7.912 (2H, d), 8.66 (1H, s), 9.21 (1H, s), 9.25 (2H, s), 9.29 (4H, s).

Example 34

2-[5-amidino-2-(cyanomethoxy)phenoxy]ethyl 4-({1-amidinopiperidin-4-yl}oxy)benzoate ditrifluoroacetate The compound of Example 8 (25 mg, 0.037 mmol) and potassium carbonate (16 mg, 0.116 mmol) were suspended in dehydrated DMF (2 ml) and iodoacetonitrile (7 μl, 0.041 mmol) was added. The mixture was stirred at room temperature for 4 hours, and ice-cooled, and 1N hydrochloric acid 0.5 ml was added thereto. The mixture was concentrated under reduced pressure, and the obtained residue was purified by reversed-phase HPLC in the same manner as in Step 4 of Example 1 to give the title compound.
yield 9.8 mg (0.014 mmol, 37%)
MS (ESI, m/z) 481 (MH+)
¹H-NMR (DMSO-d₆) δ 1.60-1.72 (2H, m), 1.98-2.08 (2H, m), 3.32-3.43 (2H, m), 3.62-3.72 (2H, br), 4.46 (2H, br), 4.63 (2H, br), 4.79 (1H, br), 5.30 (2H, s), 7.11 (2H, d), 7.36 (1H, d), 7.48 (4H, s), 7.54 (1H, dd), 7.60 (1H, d), 7.91 (2H, d), 9.16 (1H, s), 9.21 (2H, s), 9.22 (4H, s).

Example 35

2-{3-amidino-5-hydroxyphenoxy}ethyl 4-[imino(pyrrolidin-1-yl)methyl]benzoate ditrifluoroacetate Step 1. Synthesis of 3-(benzyloxy)-5-hydroxybenzonitrile.
Using 3,5-dihydroxybenzonitrile instead of 3,4-dihydroxybenzonitrile and in the same manner as in Step 1 of Example 6, the title compound was obtained.
yield 756 mg (3.36 mmol, 23%)
MS (ESI, m/z) 225 (MH+)
Step 2. Synthesis of 3-(benzyloxy)-5-hydroxybenzamidine trifluoroacetate.
Using 3-(benzyloxy)-5-hydroxybenzonitrile instead of 4-(benzyloxy)-3-hydroxybenzonitrile and in the same manner as in Step 2 of Example 6, the title compound was obtained.
yield 506 mg (1.42 mmol, 43%)
MS (ESI, m/z) 242 (MH+)
¹H-NMR (DMSO-d₆) δ 5.13 (2H, s), 6.75-6.77 (2H, m), 6.89 (1H, s), 7.31-7.46 (5H, m), 9.10 (2H, s). 9.22 (2H, s).
Step 3. Synthesis of 2-{3-amidino-5-hydroxyphenoxy}ethyl 4-[imino(pyrrolidin-1-yl)methyl]benzoate ditrifluoroacetate.
Using 3-(benzyloxy)-5-hydroxybenzamidine trifluoroacetate instead of 4-(benzyloxy)-3-hydroxybenzamidine trifluoroacetate and in the same manner as in Step 3 of Example 6, the title compound was obtained.
yield 60.0 mg (0.0961 mmol, 17%)
MS (ESI, m/z) 396 (MH+)
¹H-NMR (DMSO-d₆) δ 1.84 (2H, quint), 2.03 (2H, quint), 3.31 (2H, t), 3.53 (2H, t), 4.37 (2H, br), 4.65 (2H, br), 6.69-6.70 (1H, m), 6.77 (1H, s), 6.84 (1H, s), 7.77 (2H, d), 8.12 (2H, d), 8.91 (1H, s), 9.13 (2H, s), 9.19 (2H, s), 9.36 (2H, s).

Example 36

{3-amidino-5-[2-({4-[imino(pyrrolidin 1-yl)methyl]benzoyl}oxy)ethoxy]phenoxy}acetic acid ditrifluoroacetate.

Step 1. Synthesis of 2-{3-amidino-5-[benzyloxycarbonylmethoxy]phenoxy}ethyl 4-[iminopyrrolidin-1-yl)methyl]benzoate trifluoroacetate.
Using the compound of Example 35 instead of the compound of Example 8 and in the same manner as in Step 1 of Example 15, the title compound was obtained.
yield 2.3 mg; (0.00298 mmol) yield 7.5%
MS (ESI, m/z) 544 (MH+)
Step 2. Synthesis of {3-amidino-5-[2-({4-[iminopyrrolidin-1-yl)methyl]benzoyl}oxy)ethoxy]phenoxy}acetic acid ditrifluoroacetate.

Using 2-{3-amidino-5-[benzyloxycarbonylmethoxy]phenoxy}ethyl 4-[imino(pyrrolidin-1-yl)methyl]benzoate trifluoroacetate instead of 2-{5-amidino-2-benzyloxycarbonylmethoxy}ethyl 4-({1-amidinopiperidin-4-yl}oxy)benzoate ditrifluoroacetate and in the same manner as in Step 2 of Example 15, the title compound was obtained.

yield 3.76 mg (0.00551 mmol) yield quantitative
MS (ESI, m/z) 454 (MH+)
$^1$H-NMR (DMSO-$d_6$) δ 1.84 (2H, quint), 2.03 (0.2H, quint), 3.31 (2H, t), 3.53 (2H, t), 4.43 (2H, br), 4.66 (2H, br), 4.77 (2H, s), 6.90 (1H, m), 7.01 (1H, s), 7.06 (1H, s), 7.77 (2H, d), 8.12 (2H, d), 8.92 (1H, s), 9.23 (2H, s), 9.28 (2H, s), 9.38 (1H, s).

Example 37

2-(3-amidinophenoxy)ethyl 6-[imino(pyrrolidin-1-yl)methyl]nicotinate tritrifluoroacetate Step 1. Synthesis of 6-[imino(pyrrolidin-1-yl)methyl]nicotinic acid dihydrochloride.

6-Cyanonicotinic acid (4.15 g, 28.0 mmol) was dissolved in anhydrous ethanol (3.2 ml) and 4N hydrochloric acid/1,4-dioxane (30 ml), and the mixture was stirred in a closed system at room temperature for two nights. The solvent was evaporated under reduced pressure, and the obtained residue was suspended in anhydrous ethanol (90 ml). Pyrrolidine (2.34 ml, 28.0 mmol) was added thereto, and the mixture was stirred at room temperature for 3 days. Pyrrolidine (3.51 ml, 42.0 mmol) was added again, and the mixture was stirred for 2.5 hours. The solvent was evaporated under reduced pressure, and water aid ethanol were added to the obtained residue. The precipitate was removed by filtration, ethanol was evaporated under reduced pressure, and the obtained aqueous solution was lyophilized to give the title compound without purification operation.

yield 10.0 g (34.5 mmol) yield quantitative
MS (ESI, m/z) 220 (MH+)

Step 2. Synthesis of 2-bromoethyl 6-[imino(pyrrolidin-1-yl)methyl]nicotinate ditrifluoroacetate.

6-[Imino(pyrrolidin-1-yl)methyl]nicotinic acid dihydrochloride (10.0 g, 34.5 mmol) obtained in Step 1 was dissolved in 2-bromoethanol (50 ml), p-toluenesulfonic acid monohydrate (856 mg, 4.5 mmol) was added thereto, and the mixture was stirred at 85° C. for two nights. The solvent was evaporated under reduced pressure, and the obtained residue was purified by reversed-phase HPLC in the same manner as in Step 4 of Example 1 to give the title compound.

yield 1.27 g (2.29 mmol, 7%)
MS (ESI, m/z) 326 (MH+)
$^1$H-NMR (DMSO-$d_6$) δ 1.89 (2H, quint), 2.06 (2H, quint), 3.47 (2H, t), 3.61 (2H, t), 3.87 (2H, t), 4.70 (2H, t), 8.01 (1H, d), 8.60 (1H, dd), 9.13 (1H, s), 9.25 (1H, m), 9.57 (1H, s).

Step 3. Synthesis of 2-(3-amidinophenoxy)ethyl 6-[imino(pyrrolidin-1-yl)methyl]nicotinate tritrifluoroacetate.

3-Hydroxybenzamidine trifluoroacetate (152 mg, 0.606 mmol) obtained in Step 1 of Example 2,2-bromoethyl 6-[imino(pyrrolidin-1-yl)methyl]nicotinate ditrifluoroacetate. (345 mg, 0.606 mmol) obtained in Step 2, and cesium carbonate (790 mg, 2.42 mmol) were stirred at 50° C. overnight in anhydrous N,N-dimethylformamide (6 ml). 1N Hydrochloric acid (4.5 ml) was added to the mixture under ice-cooling, the solvent was evaporated under reduced pressure, and the obtained residue was purified by reversed-phase HPLC in the same manner as in Step 4 of Example 1 to give the title compound.

yield 24.1 mg, (0.0356 mmol, 6%)
MS (ESI, m/z) 382 (MH+)
$^1$H-NMR (DMSO-$d_6$) δ 1.88 (2H, quint), 2.06 (2H, quint), 3.45 (2K t), 3.61 (2×t), 4.49 (2H, m), 4.74 (2H, m), 7.33-7.58 (4H, m), 7.99 (1H, d), 8.58 (1H, dd), 9.17 (1H, s), 9.22 (1H, m), 9.32 (4H, s), 9.60 (1H, s).

The structural formulas of the compounds described in the Examples are shown in Table 1. In the formulas, TFA means trifluoroacetic acid.

TABLE 1 compound of Ex. 1

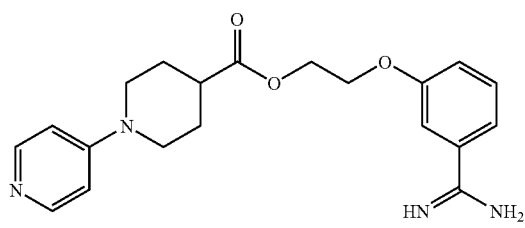

2TFA compound of Ex. 2

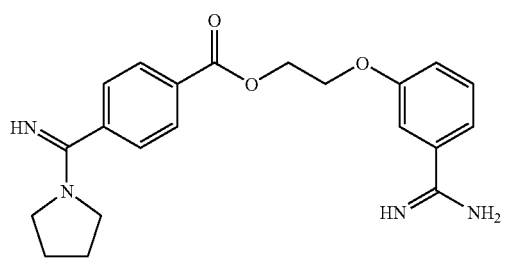

2TFA

TABLE 1-continued
compound of Ex. 3
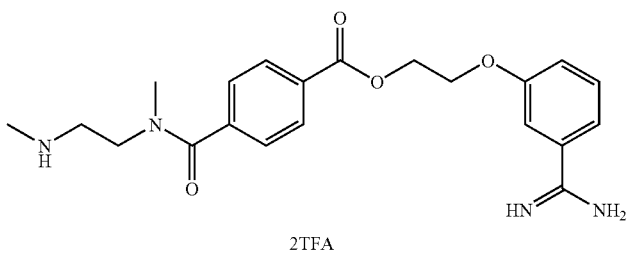
2TFA
compound of Ex. 4
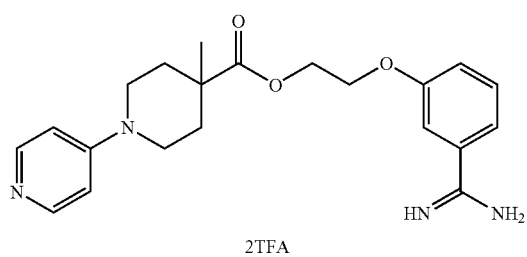
2TFA
compound of Ex. 5
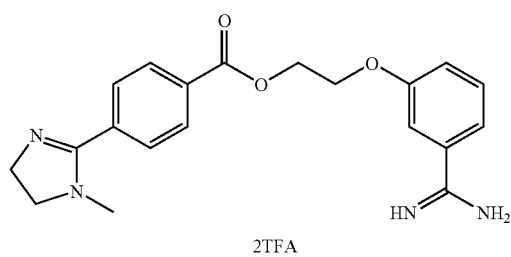
2TFA
compound of Ex. 6
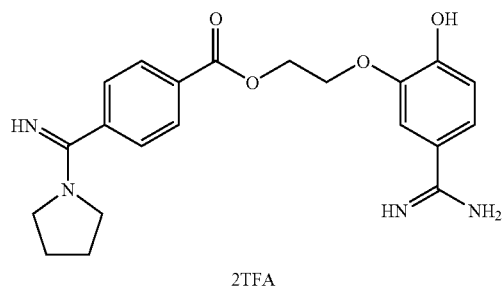
2TFA
compound of Ex. 7
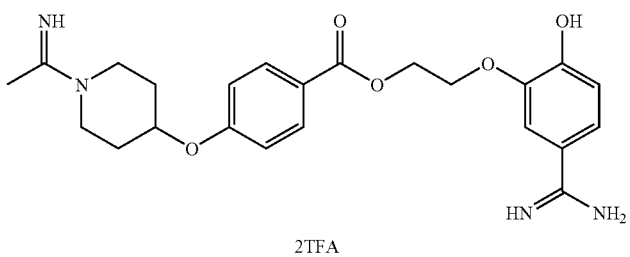
2TFA
compound of Ex. 8
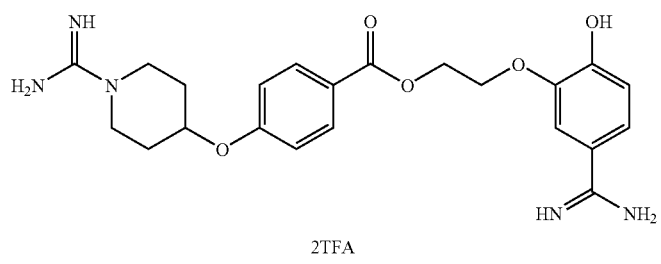
2TFA TABLE 1-continued
compound of Ex. 9
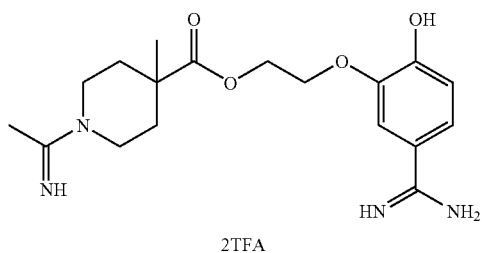
2TFA
compound of Ex. 10
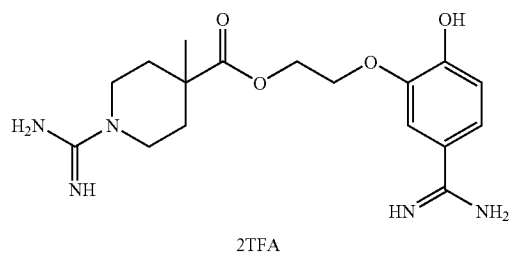
2TFA
compound of Ex. 11
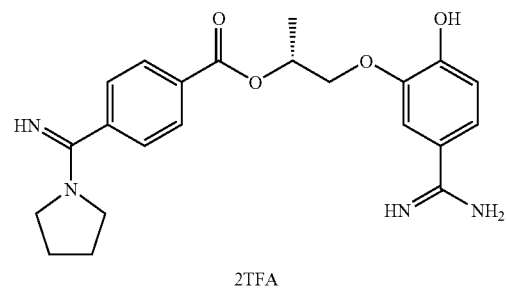
2TFA
compound of Ex. 12
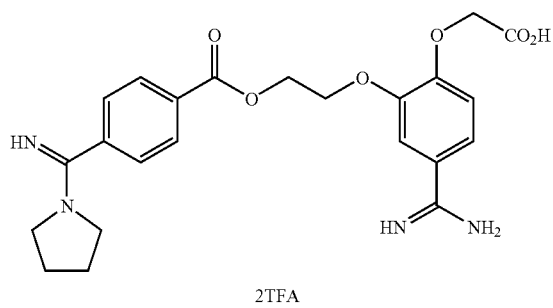
2TFA
compound of Ex. 13
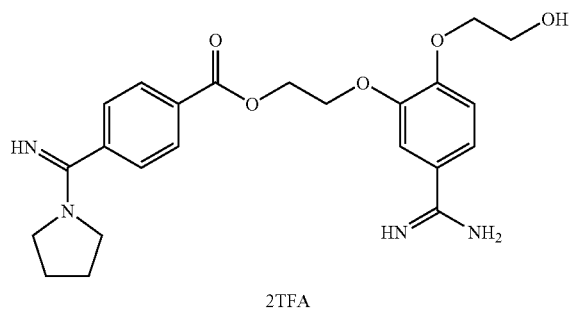
2TFA TABLE 1-continued
compound of Ex. 14
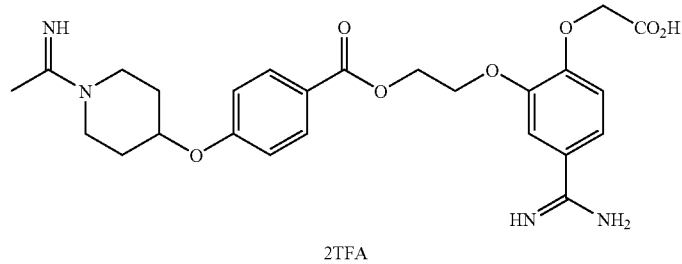
2TFA
compound of Ex. 15
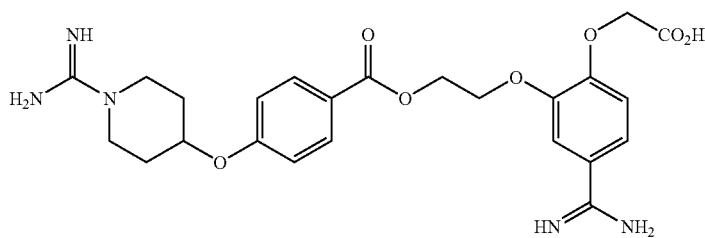
2TFA
compound of Ex. 16
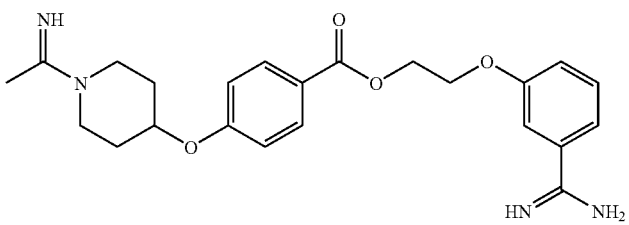
2TFA
compound of Ex. 17
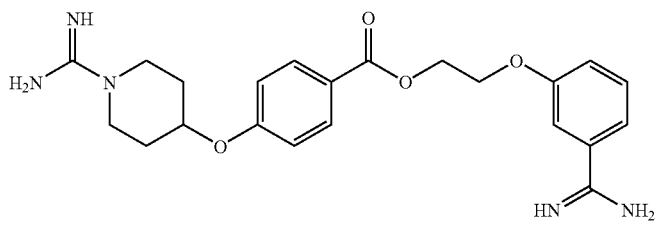
2TFA
compound of Ex. 18
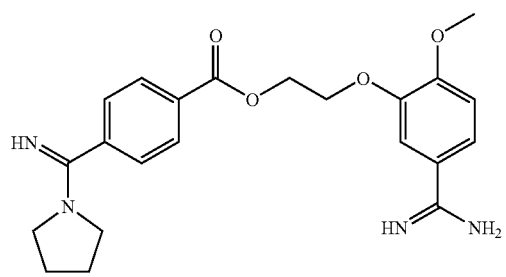
2TFA TABLE 1-continued
| compound of Ex. 19 | 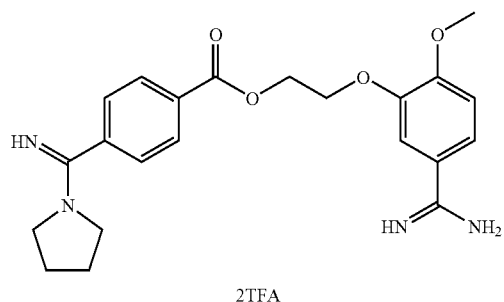 |
| --- | --- |
| | 2TFA |
| compound of Ex. 20 | 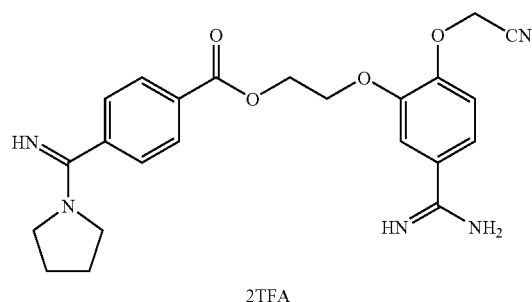 |
| | 2TFA |
| compound of Ex. 21 | 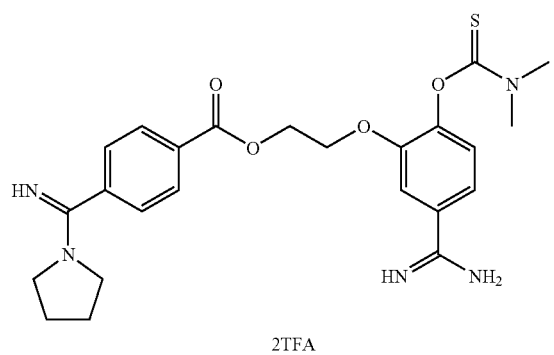 |
| | 2TFA |
| compound of Ex. 22 | 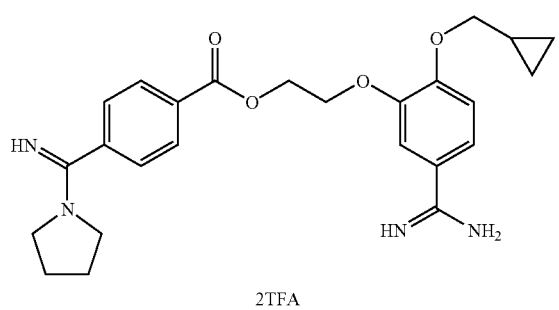 |
| | 2TFA |
| compound of Ex. 23 | 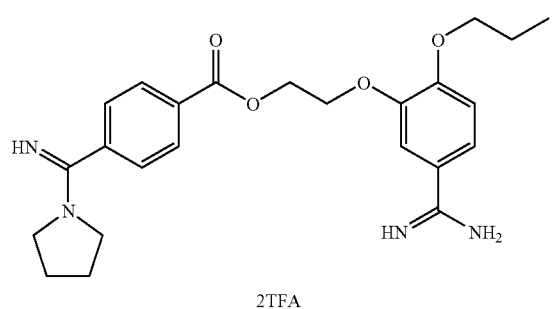 |
| | 2TFA |

TABLE 1-continued
compound of Ex. 24
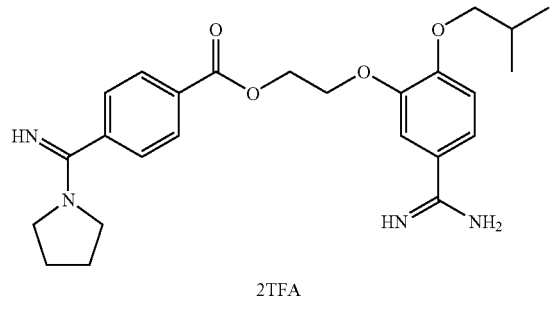
2TFA
compound of Ex. 25
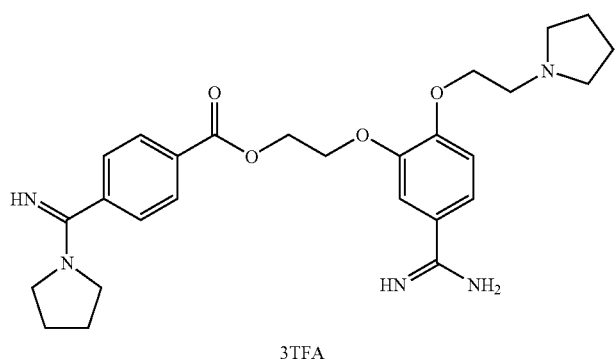
3TFA
compound of Ex. 26
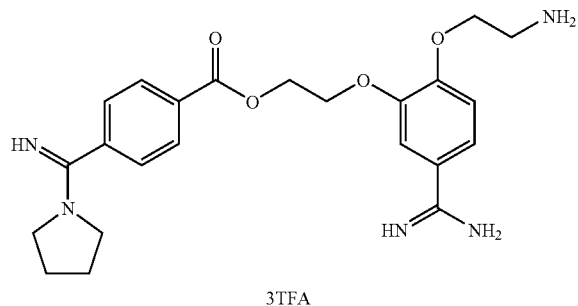
3TFA
compound of Ex. 27
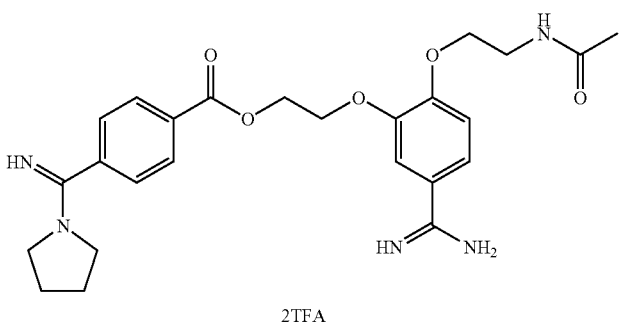
2TFA TABLE 1-continued
compound of Ex. 28
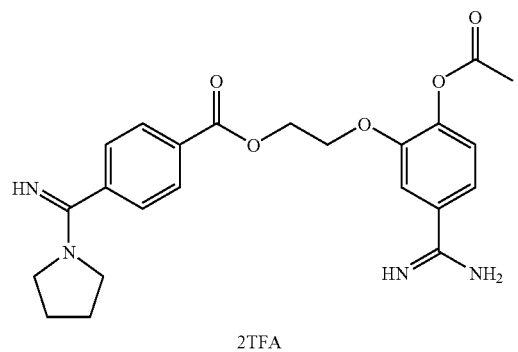
2TFA
compound of Ex. 29
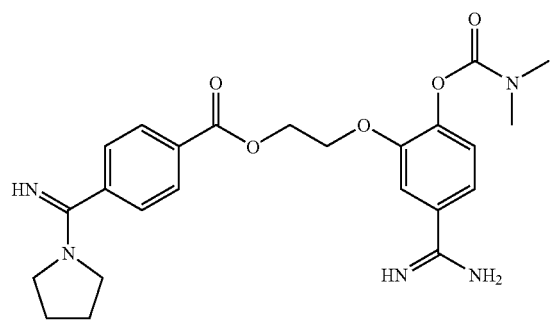
2TFA
compound of Ex. 30
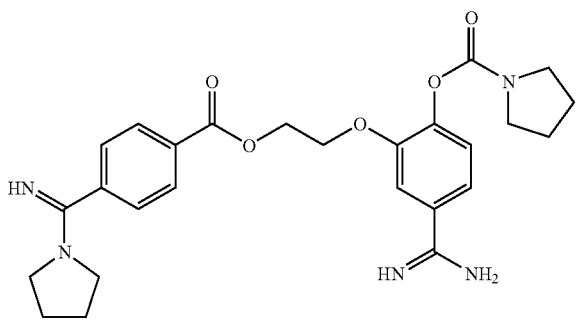
2TFA
compound of Ex. 31
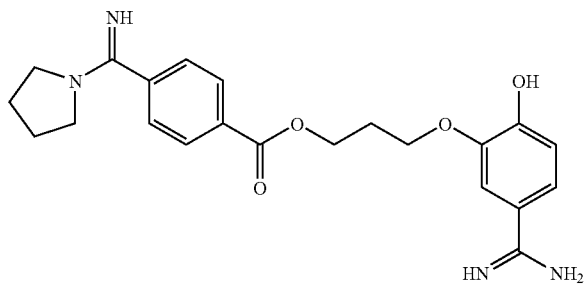
2TFA TABLE 1-continued
compound of Ex. 32
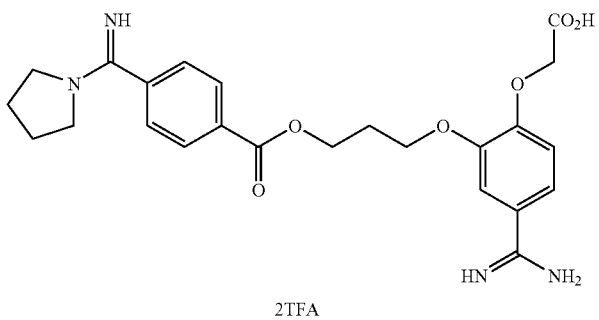
2TFA
compound of Ex. 33
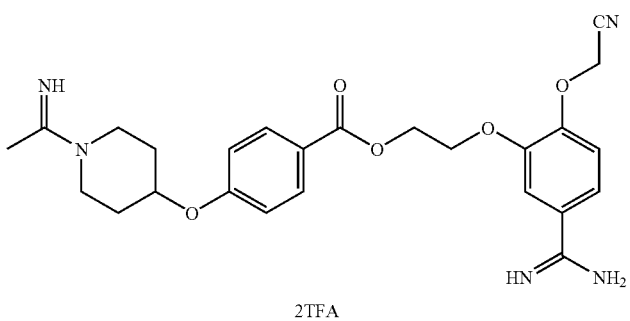
2TFA
compound of Ex. 34
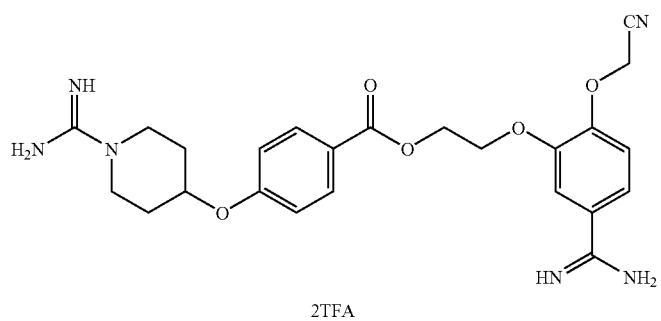
2TFA
compound of Ex. 35
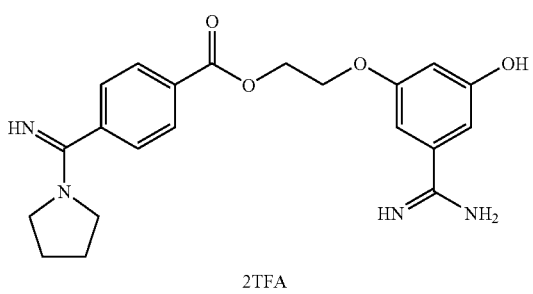
2TFA
compound of Ex. 36
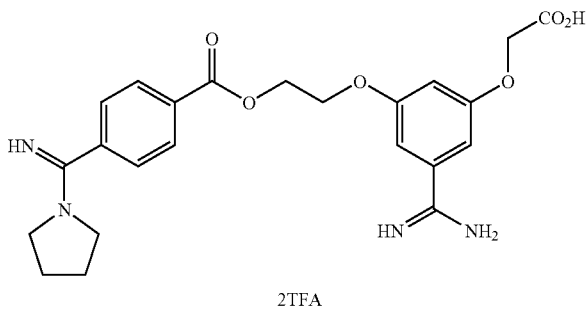
2TFA TABLE 1-continued compound of Ex. 37

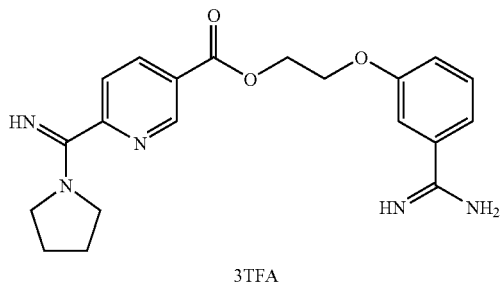

3TFA

Experimental Example 1

Determination of Activated Factor X Activity-Inhibitory Activity

Using a 96 well plate (#3396, Costar), 0.015 U/ml FXa (10 μL) and a test compound (10 μL) were blended with 100 mM Tris-HCl buffer (130 μL) containing 0.02% Tween 20, 0.1% PEG6000 and 0.2 M NaCl for 10 minutes, and a substrate for color development (0.2 mM S-2222 50 μL) was added thereto. Using a Microplate reader Benchmark Plus (BIO-RAD), the reaction rate was measured from the time course changes at absorbance 405 nm. The reaction rate of the control was taken as 100% and the negative logarithm of the concentration capable of suppressing 50% of the reaction rate of the control was taken as the $pIC_{50}$ value. The results are shown in Table 2.

Experiment Example 2

Determination of Activated Factor II (FIIa, Thrombin)-Inhibitory Activity

Using a 96 well plate (#3396, Costar), 0.125 U/ml activated factor IIa (thrombin) (10 μL) and a test compound (10 μL) were blended with 100 mM Tris-HCl buffer (130 μL) containing 0.02% Tween 20, 0.1% PEG6000 and 0.2 M NaCl for 10 minutes, and a substrate for color development (0.1 mM S-2238 50 μL) was added thereto. Using a Microplate reader Benchmark Plus (BIO-RAD), the reaction rate was measured from the time course changes at absorbance 405 nm. The reaction rate of the control was taken as 100% and the negative logarithm of the concentration capable of suppressing 50% of the reaction rate of the control was taken as the $pIC_{50}$ value. The results are shown in Table 2.

Experimental Example 3

Determination of Anticoagulant Activity

The aPTT measurement method using an automatic blood coagulation time measuring device, Sysmex CA-3000 (TOA Medical Electronics Co., Ltd.) was performed. A solution (5 μl) of the test compound was placed in a sample tube (SU-40, TOA Medical Electronics Co., Ltd.), human plasma (hemolyance coagulation control I, iatron Laboratory, 45 μl) was added and the mixture was incubated at 37° C. for 3 minutes. To the plasma solution were added dataphay•APTT (rabbit brain-derived cephalin, DADE Behring Co., Ltd., 50 μl) and 0.02 M calcium chloride (50 μl), and the time up to the coagulation of plasma was automatically measured. The anticoagulation activity is shown as the negative logarithm of the concentration prolonging the aPTT of the control to two-fold (paPTT2). The results are shown in Table 2.

Experimental Example 4

Evaluation of Stability in Plasma

A 100 μM solution (5 μl) of the test compound was added to human plasma (495 μl) (final drug concentration, 10 μM), and the mixture was incubated at 37° C. Samples (each 50 μl) were taken at 0 minutes, 3 minutes, 10 minutes, and 20 minutes after addition of the drug solution, diluted with distilled water (50 μl), and the reaction was quenched by adding 100% acetonitrile (300 μl) and blending them. After deproteinization by centrifugation at 15000 rpm for 5 minutes, the mixture was concentrated to dryness by a centrifugal evaporator. The sample was dissolved in 120 μl of 0.1% aqueous TFA, the peak area or height of the test compound was calculated by HPLC, and the disappearance half-life was determined. The results are shown in Table 2 ($T_{1/2}$).

TABLE 2

| | $pIC_{50}$ (FXa) | $pIC_{50}$ (IIa) | paPTT2 | $T_{1/2}$ (minutes) |
|---|---|---|---|---|
| compound of Ex. 6 | 8.5 | 4.1 | 6 | 1.6 |
| compound of Ex. 13 | 7.8 | 4.2 | 6.4 | 2.7 |
| compound of Ex. 16 | 7.2 | <4.0 | 5.4 | 1.7 |
| compound of Ex. 17 | 7.2 | <4.0 | 5.1 | 5.6 |
| compound of Ex. 18 | 6.6 | <4.0 | 5.2 | 1.1 |
| compound of Ex. 20 | 7.9 | 5.2 | 6.1 | 2.1 |
| compound of Ex. 24 | 7.4 | 4.9 | 5.8 | 0.7 |
| compound of Ex. 28 | 8.4 | 5.8 | 6.4 | 3.5 |
| compound of Ex. 37 | 6.7 | <4.0 | 5.2 | N.T. |

Experimental Example 5

Evaluation of Dog Dialysis Model

1. Surgical Operation.

Beagles (♂, 11 kg-15 kg, Nosan Corp., Japan) were anesthetized with pentobarbital (30 mg/kg, Tokyo Chemical Industry Co., Ltd.) by intravenous administration from the cephalic vein of the forefoot. A tracheostomy tube was inserted and artificial breathing was started. Placing needles [14G (serflow placing needle, Termo Corp.), 16G (happycath, Medikit Co., Led), 18G (serflow placing needle, Termo Corp.)] were punctured into the left femoral vein, right femoral artery, and right cephalic vein of the forefoot, respectively, and an outer shunt (Senko Medical Instrument Mfg. CO., Ltd.) filled with saline was set to the femoral vein and artery. For hemodialysis, a hemodialysis device for one person (DBG-01, Nikkiso Co., Ltd.), a hollow fiber dialyzer (FB-50, triacetate (CTA) film, Nipro Corp.) and sodium bicarbonate dialysate (AK-sorita•DL, Shimizu Corp.) were used.

2. Experiment Procedure.

The experiment was performed under the conditions of blood flow 80 ml/minute, dialysate flow 300 ml/minute, water removal amount 0 ml/minute. During dialysis, pentobarbital (12 mg/kg/hour) was continuously administered from the cephalic vein of the forefoot to maintain anesthesia. The control and test compounds were continuously administered into the arterial blood circuit (B) at 5 ml/hour.

For the antithrombus action, suppression of an increase in the arterial circuit pressure was used as an index, and the dialysis time was up to the time point when the arterial circuit pressure reached 300 mmHg or 4 hours after the start of the dialysis. In addition, the bleeding time at 2 hour after the start of the administration (15 minutes later for the control since it does not reach 2 hours) was measured by the Template method.

Figure 2:
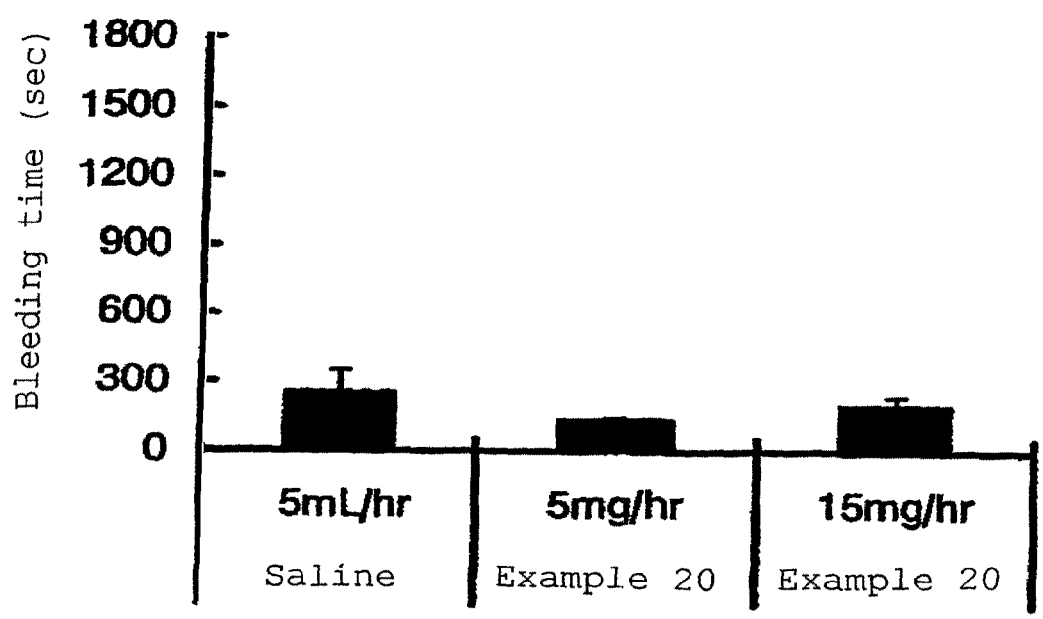
FIG. 2 shows the bleeding time in the dog dialysis models.

As shown in FIG. 1, the compound of Example 20 suppressed an increase in the arterial circuit pressure, and the dialysis was possible for 4 hours. In addition, the bleeding time of the compound of Example 20 was of the same level as the control (FIG. 2).

From the foregoing results, the compound of the present invention is considered to be usable for the prevention of blood circuit coagulation during extracorporeal blood circulation, and become a safe therapeutic drug free of a blood bleeding prolongation action.

Industrial Applicability

A compound represented by the formula (1) and a pharmaceutically acceptable salt thereof have a high FXa inhibitory activity and anticoagulant action, as shown in the aforementioned Experimental Examples, and can be used as activated blood coagulation factor X inhibitors/anticoagulants for various diseases in which an FXa-dependent coagulation process is involved in the pathology. For example, they can be used as therapeutic or prophylactic drugs for any of thrombus formation during extracorporeal blood circulation, cerebral infarction, cerebral thrombus, cerebral embolism, transient cerebral ischemic attack (TIA), acute and chronic myocardial infarction, unstable angina pectoris, pulmonary obliteration, peripheral arterial obstruction, deep vein thrombosis, disseminated intravascular coagulation syndrome, thrombus formation after artificial vascular prosthesis or replacement of artificial valve, reocclusion and restenosis after coronary-artery bypass surgery, reocclusion and restenosis after reconstruction of blood vessel such as percutaneous transluminal coronary angioplasty (PTCA), percutaneous transluminal coronary recanaryzation (PTCR), and the like.

Particularly, a compound represented by the formula (1) and a pharmaceutically acceptable salt thereof are useful as anticoagulants for an extracorporeal blood circuit (e.g., hemodialyzer, artificial heart lung apparatus, etc.).

In addition, a compound represented by the formula (1) and a pharmaceutically acceptable salt thereof are rapidly cleared from the blood. That is, since the serum half-life is short, hemostasis is easy when the bleeding symptom is observed during administration. Thus, they are useful as anticoagulants that can be used safely.

Moreover, a compound represented by the formula (1) shows low thrombin inhibitory activity and is an FXa selective inhibitor and anticoagulant that can be used safely from the aspect of bleeding risk.

Furthermore, a low-molecular weight FXa inhibitor, for example, a compound represented by the formula (1), is useful as an anticoagulant to be used for an extracorporeal blood circulation/extracorporeal blood circuit.

Particularly, an FXa selective low-molecular weight FXa inhibitor, for example, a compound represented by the formula (1), whose clearance from the blood is rapid, i.e., serum half-life is short, can be used safely and conveniently as an anticoagulant for an extracorporeal blood circuit that prevents blood coagulation, and is useful because a treatment of and attention to hemostasis necessary after the completion of the extracorporeal blood circulation can be clearly reduced.

The present invention can also provide a method for preventing formation of thrombus in an extracorporeal blood circuit, which method comprises incorporating a low-molecular weight FXa inhibitor as a component of the circuit.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (1-2):

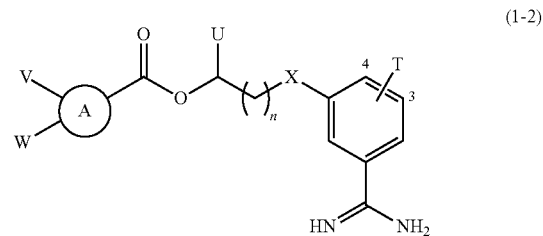

wherein, in the formula (1-2), ring A is a phenyl group;

T is a hydrogen atom, a hydroxyl group, a $C_{1-10}$ alkoxy group optionally having substituent(s), a $C_{1-10}$ acyloxy group optionally having substituent(s), a carbamoyloxy group optionally having substituent(s), a thiocarbamoyloxy group optionally having substituent(s), an amino group, a halogeno substituent, a cyano group, a nitro group, a $C_{1-10}$ alkyl group optionally having substituent(s), a $C_{1-10}$ alkylamino group optionally having substituent(s), a $C_{1-10}$ alkylthio group optionally having substituent(s), a $C_{1-10}$ acylamino group optionally having substituent(s), a carboxyl group, a $C_{2-10}$ alkoxycarbonyl group optionally having substituent(s), a carbamoyl group optionally having substituent(s), or a thiocarbamoyl group optionally having substituent(s);

U is a hydrogen atom, or a methyl group,

V is a hydrogen atom, a halogeno substituent, a hydroxyl group, a $C_{1-10}$ alkyl group optionally having substituent(s), a $C_{1-10}$ alkoxy group optionally having substituent(s), a $C_{1-10}$ alkylamino group optionally having substituent(s), a $C_{1-10}$ alkylthio group optionally having substituent(s), a cyano group, a nitro group, a carboxyl group, or a carbamoyl group optionally having substituent(s);

W is a group represented by formula (2-1):

$$HN=C(Q)- \qquad (2\text{-}1)$$

wherein:

in the formula (2-1),

Q is a 3-9 membered ring containing one nitrogen atom and having a bond at the nitrogen atom;

X is a nitrogen atom optionally substituted by a $C_{1-6}$ alkyl group, an oxygen atom, a sulfur atom, or a methylene group; and n is an integer of 1-3, or a pharmaceutically acceptable salt thereof.

2. A compound according to claim 1, wherein T is bonded to the 3-position or the 4-position of the benzamidine ring, or a pharmaceutically acceptable salt thereof.

3. A compound according to claim 2, wherein, in the formula (1-2),

X is an oxygen atom or a sulfur atom;

U is a hydrogen atom or a methyl group;

T is a hydrogen atom, a hydroxyl group, a $C_{1-10}$ alkoxy group optionally having substituent(s), a $C_{2-10}$ acyloxy group optionally having substituent(s), a carbamoyloxy group optionally having substituent(s), or a thiocarbamoyloxy group optionally having substituent(s); and n is an integer of 1-2, or a pharmaceutically acceptable salt thereof.

4. A compound according to claim 3, wherein,

V is a hydrogen atom, a halogeno substituent, or a $C_{1-6}$ alkyl group, or a pharmaceutically acceptable salt thereof.

5. A pharmaceutical composition, comprising a compound according to claim 1 or a pharmaceutically acceptable salt thereof and a pharmaceutically acceptable carrier.

6. A pharmaceutical composition, comprising a compound and according to claim 2 or a pharmaceutically acceptable salt thereof and a pharmaceutically acceptable carrier.

7. A pharmaceutical composition, comprising a compound according to claim 3 or a pharmaceutically acceptable salt thereof and a pharmaceutically acceptable carrier.

8. A pharmaceutical composition, comprising a compound according to claim 4 or a pharmaceutically acceptable salt thereof and a pharmaceutically acceptable carrier.

9. A method of inhibiting an activated blood coagulation factor X, which comprises administering to a subject or applying to an extracorporeal blood circuit an effective amount of a compound according to claim 1 or a pharmaceutically acceptable salt thereof.

10. The method of claim 9, which comprises administering an effective amount of said compound or a pharmaceutically acceptable salt thereof to a subject in need thereof.

11. The method of claim 9, which comprises applying an effective amount of said compound or a pharmaceutically acceptable salt thereof to an extracorporeal blood circuit.

12. A method for reducing coagulation, which comprises administering to a subject or applying to an extracorporeal blood circuit an effective amount of a compound according to claim 1 or a pharmaceutically acceptable salt thereof.

13. The method of claim 12, which comprises administering an effective amount of said compound or a pharmaceutically acceptable salt thereof to a subject in need thereof.

14. The method of claim 12, which comprises applying an effective amount of said compound or a pharmaceutically acceptable salt thereof to an extracorporeal blood circuit.

15. A pharmaceutical solution or dispersion, comprising a compound according to claim 1 or a pharmaceutically acceptable salt thereof.

16. A pharmaceutical solution or dispersion, comprising a compound according to claim 2 or a pharmaceutically acceptable salt thereof.

17. A pharmaceutical solution or dispersion, comprising a compound according to claim 3 or a pharmaceutically acceptable salt thereof.

18. A pharmaceutical solution or dispersion, comprising a compound according to claim 4 or a pharmaceutically acceptable salt thereof.

19. A compound, which is 2-[5-amidino-2-(cyanomethoxy)-phenoxy]ethyl 4-[imino(pyrrolidin-1-yl)methyl]benzoate or a pharmaceutically acceptable salt thereof.

20. A pharmaceutical composition, comprising the compound according to claim 19 or a pharmaceutically acceptable salt thereof and a pharmaceutically acceptable carrier.

21. A method of inhibiting an activated blood coagulation factor X, which comprises administering to a subject or applying to an extracorporeal blood circuit an effective amount of the compound according to claim 19 or a pharmaceutically acceptable salt thereof.

22. A method for reducing coagulation, which comprises administering to a subject or applying to an extracorporeal blood circuit an effective amount of the compound according to claim 19 or a pharmaceutically acceptable salt thereof.

23. A pharmaceutical solution or dispersion, comprising the compound according to claim 19 or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,227,506 B2 | Page 1 of 1 |
| APPLICATION NO. | : 11/832895 | |
| DATED | : July 24, 2012 | |
| INVENTOR(S) | : Masaru Takayanagi et al. | |

It is certified that error appears in the above-identified patent and that said Letters Patent is hereby corrected as shown below:

On the title page, Item 73, the spelling of the assignee is incorrect. Item 73 should read:

-- (73) Assignee: Ajinomoto Co., Inc., Tokyo (JP) --

Signed and Sealed this
Twenty-fifth Day of September, 2012

David J. Kappos
*Director of the United States Patent and Trademark Office*

UNITED STATES PATENT AND TRADEMARK OFFICE
CERTIFICATE OF CORRECTION

PATENT NO.         : 8,227,506 B2
APPLICATION NO.    : 11/832895
DATED              : July 24, 2012
INVENTOR(S)        : Masaru Takayanagi et al.

It is certified that error appears in the above-identified patent and that said Letters Patent is hereby corrected as shown below:

Column 63, line 20, Claim 2, "bcnzamidine" should read "benzamidine"

Column 63, lines 40-41, Claim 6, "compound and according to claim 2" should read "compound according to claim 2"

Signed and Sealed this
First Day of January, 2013

David J. Kappos
*Director of the United States Patent and Trademark Office*